US008257395B2

(12) United States Patent
Bhatnagar et al.

(10) Patent No.: US 8,257,395 B2
(45) Date of Patent: Sep. 4, 2012

(54) SPINAL FIXATION WITH SELECTIVELY APPLIED BONE GROWTH PROMOTING AGENT

(75) Inventors: Mohit K. Bhatnagar, Potomac, MD (US); Jack Y. Yeh, North Potomac, MD (US)

(73) Assignee: JMEA Corporation, Rockville, MD (US)

( * ) Notice: Subject to any disclaimer, the term of this patent is extended or adjusted under 35 U.S.C. 154(b) by 590 days.

(21) Appl. No.: 11/859,386

(22) Filed: Sep. 21, 2007

(65) Prior Publication Data

US 2009/0082810 A1 Mar. 26, 2009

(51) Int. Cl.
*A61B 17/70* (2006.01)

(52) U.S. Cl. .......... 606/246; 606/265; 606/907

(58) Field of Classification Search .......... 606/60, 606/246, 250–279
See application file for complete search history.

(56) References Cited

U.S. PATENT DOCUMENTS

| 3,605,123 | A |   | 9/1971  | Hahn           |        |
|-----------|---|---|---------|----------------|--------|
| 4,177,524 | A |   | 12/1979 | Grell et al.   |        |
| 4,714,469 | A |   | 12/1987 | Kenna          |        |
| 4,834,757 | A |   | 5/1989  | Brantigan      |        |
| 5,098,434 | A |   | 3/1992  | Serbousek      |        |
| 5,190,545 | A | * | 3/1993  | Corsi et al.   | 606/74 |
| 5,306,275 | A |   | 4/1994  | Bryan          |        |
| 5,348,026 | A |   | 9/1994  | Davidson       |        |
| 5,360,448 | A |   | 11/1994 | Thramann       |        |
| 5,405,389 | A |   | 4/1995  | Conta et al.   |        |
| 5,505,736 | A |   | 4/1996  | Reimels et al. |        |
| 5,545,165 | A | * | 8/1996  | Biedermann et al. | 606/261 |
| 5,571,139 | A |   | 11/1996 | Jenkins, Jr.   |        |
| 5,785,710 | A |   | 7/1998  | Michelson      |        |
| 6,206,924 | B1 |  | 3/2001  | Timm           |        |
| 6,264,656 | B1 |  | 7/2001  | Michelson      |        |
| 6,277,120 | B1 |  | 8/2001  | Lawson         |        |
| 6,605,089 | B1 |  | 8/2003  | Michelson      |        |
| 6,790,233 | B2 |  | 9/2004  | Brodke et al.  |        |
| 7,281,925 | B2 |  | 10/2007 | Hall           |        |
| 2002/0138144 | A1 | | 9/2002 | Michelson |         |
| 2002/0173850 | A1 | | 11/2002 | Brodke et al. |      |
| 2004/0034351 | A1 | * | 2/2004 | Sherman et al. | 606/61 |
| 2004/0087950 | A1 | | 5/2004 | Teitelbaum |         |
| 2004/0215341 | A1 | * | 10/2004 | Sybert et al. | 623/13.17 |
| 2004/0225360 | A1 | | 11/2004 | Malone |           |
| 2004/0253185 | A1 | * | 12/2004 | Herweck et al. | 424/10.2 |
| 2005/0004573 | A1 | * | 1/2005 | Abdou | 606/61 |
| 2005/0015088 | A1 | * | 1/2005 | Ringeisen | 606/69 |

(Continued)

FOREIGN PATENT DOCUMENTS

EP 0532421 3/1993

(Continued)

OTHER PUBLICATIONS

International Search Report and Written Opinion, mailed Jun. 4, 2009, from PCT Application No. PCT/US2008/061408.

(Continued)

*Primary Examiner* — Eduardo C Robert
*Assistant Examiner* — Jerry Cumberledge
(74) *Attorney, Agent, or Firm* — Plumsea Law Group, LLC

(57) ABSTRACT

A spinal fixation system including a selectively applied bone growth promoting agent is disclosed. The types of spinal fixation systems which may include a selectively applied bone growth promoting agent include systems comprised of rods, plates, screws, and hooks as well as other types of prostheses.

29 Claims, 28 Drawing Sheets

U.S. PATENT DOCUMENTS

| | | |
|---|---|---|
| 2005/0015154 A1 | 1/2005 | Lindsey et al. |
| 2005/0038512 A1 | 2/2005 | Michelson |
| 2005/0065604 A1 | 3/2005 | Stoll |
| 2005/0075645 A1 | 4/2005 | Eckman |
| 2005/0090822 A1* | 4/2005 | DiPoto ............ 606/61 |
| 2005/0187555 A1 | 8/2005 | Biedermann et al. |
| 2005/0187626 A1 | 8/2005 | McKay et al. |
| 2006/0036322 A1 | 2/2006 | Reiley |
| 2006/0041262 A1 | 2/2006 | Calvert et al. |
| 2006/0085009 A1 | 4/2006 | Truckai et al. |
| 2006/0093646 A1 | 5/2006 | Cima et al. |
| 2006/0111715 A1* | 5/2006 | Jackson ............ 606/61 |
| 2006/0149255 A1 | 7/2006 | Doubler et al. |
| 2006/0173542 A1 | 8/2006 | Shikinami |
| 2006/0190080 A1 | 8/2006 | Danoff et al. |
| 2006/0229615 A1* | 10/2006 | Abdou ............ 606/61 |
| 2006/0241623 A1 | 10/2006 | Lim et al. |
| 2006/0241776 A1 | 10/2006 | Brown et al. |
| 2006/0264948 A1* | 11/2006 | Williams ............ 606/69 |
| 2006/0264950 A1 | 11/2006 | Nelson et al. |
| 2006/0276788 A1 | 12/2006 | Berry et al. |
| 2007/0055373 A1 | 3/2007 | Hudgins et al. |
| 2007/0083265 A1 | 4/2007 | Malone |
| 2007/0173938 A1 | 7/2007 | Sweeney |
| 2007/0233071 A1* | 10/2007 | Dewey et al. ............ 606/61 |
| 2007/0270812 A1* | 11/2007 | Peckham ............ 606/61 |
| 2007/0270821 A1 | 11/2007 | Trieu et al. |
| 2007/0270858 A1* | 11/2007 | Trieu et al. ............ 606/73 |
| 2008/0154378 A1 | 6/2008 | Pelo |
| 2008/0161927 A1 | 7/2008 | Savage et al. |

FOREIGN PATENT DOCUMENTS

| | | |
|---|---|---|
| JP | 2209148 | 8/1990 |
| JP | 7275268 | 10/1995 |

OTHER PUBLICATIONS

International Search Report and Written Opinion, mailed Jun. 4, 2009, from PCT Application No. PCT/US2008/061397.
Final Office Action mailed Sep. 24, 2010 in U.S. Appl. No. 11/740,181.
Final Office Action mailed Sep. 21, 2010 in U.S. Appl. No. 11/840,707.
Office Action mailed Dec. 29, 2009 in U.S. Appl. No. 11/740,181.
Response to Office Action filed Jan. 27, 2010 in U.S. Appl. No. 11/740,181.
Office Action mailed Apr. 21, 2010 in U.S. Appl. No. 11/740,181.
Response to Office Action filed Jul. 19, 2010 in U.S. Appl. No. 11/740,181.
Office Action mailed Mar. 10, 2010 in U.S. Appl. No. 11/840,707.
Response to Office Action filed Jun. 10, 2010 in U.S. Appl. No. 11/840,707.
Interview Summary mailed Jul. 6, 2010 in U.S. Appl. No. 11/840,707.

\* cited by examiner

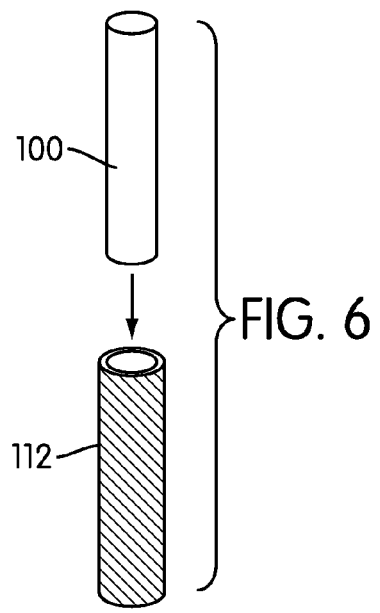
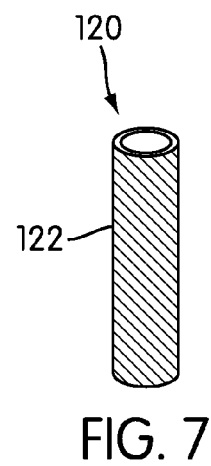
FIG. 6  FIG. 7
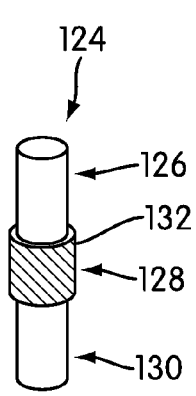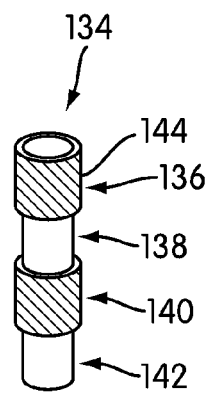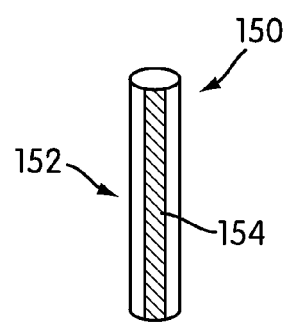
FIG. 8  FIG. 9  FIG. 10
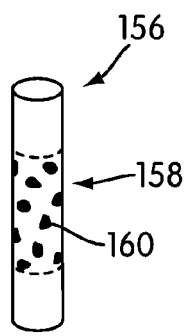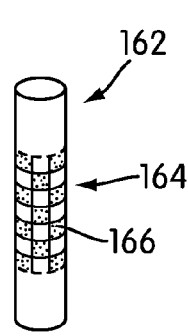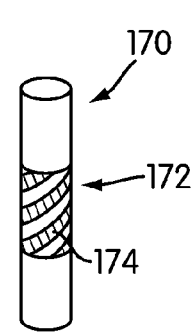
FIG. 11  FIG. 12  FIG. 13

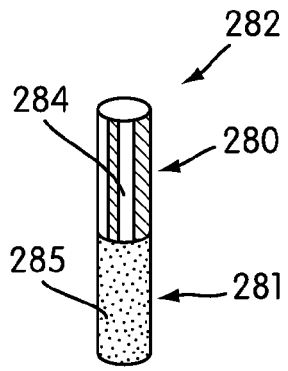 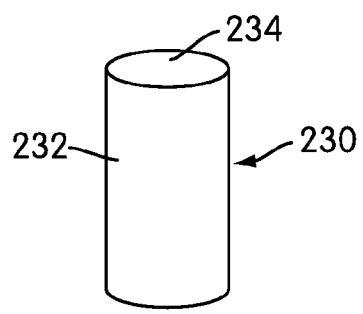 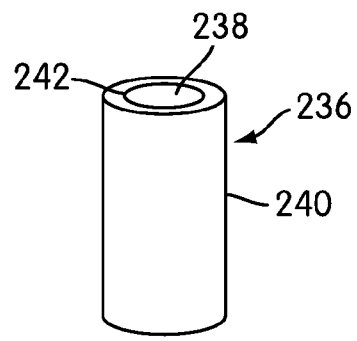
FIG. 23    FIG. 24    FIG. 25
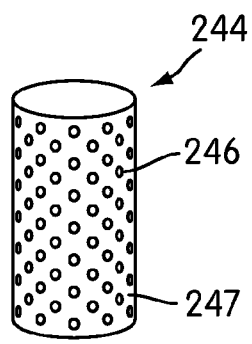
FIG. 26
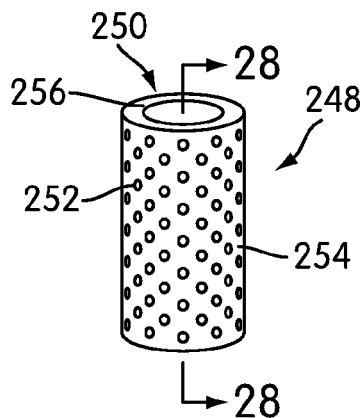 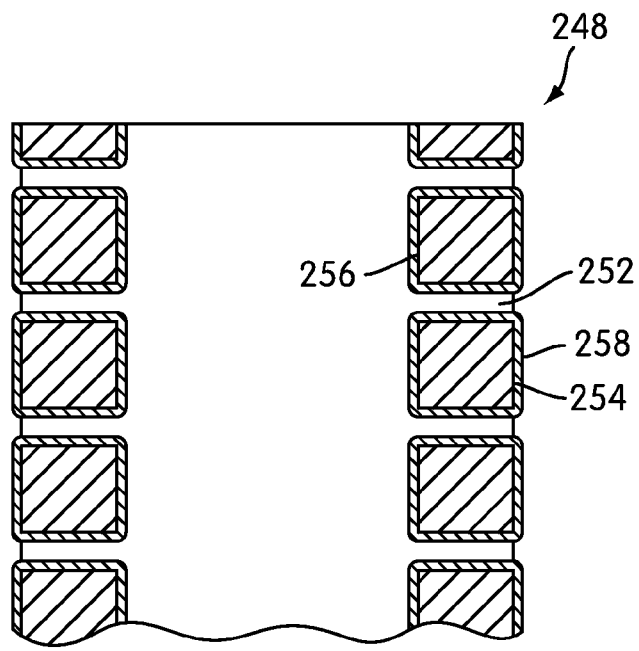
FIG. 27    FIG. 28

SPINAL FIXATION WITH SELECTIVELY APPLIED BONE GROWTH PROMOTING AGENT

BACKGROUND OF THE INVENTION

1. Field of the Invention

The present invention relates generally to spinal fixation systems and in particular to spinal fixation systems including a selectively applied bone growth promoting agent.

2. Description of Related Art

Spinal fusion implants have been previously proposed and utilized in cervical thorastic, lumbar and sacral regions. Currently, these fixation systems are utilized to hold various segments of the spine together allowing for fusion to occur. These implant systems include plates, screws, rods, hooks and cables utilized for the anterior, posterior as well as lateral portions of the spine. All these systems utilize inert materials, mostly metal, to fix the bone and allow the natural process of healing to occur. None of these systems in use actually encourage the growth of bone to facilitate the fusion or healing. Furthermore, none of these systems utilize healing processes to heal to the actual implant by providing a re-bar effect and better fixation.

One type of spinal fusion implant, the threaded spinal implant (commonly referred to as a spinal screw), may include provisions for promoting bone growth through the cage. This type of prosthesis is disclosed in Michelson (U.S. Pat. No. 6,264,656), the entirety of which is incorporated by reference. The threaded spinal implant is inserted between two adjacent vertebrae and is incorporated into the fusion of the bone along this portion of the spine.

Brantigan (U.S. Pat. No. 4,834,757) discloses plugs, used as spinal fusion implants, the entirety of which is incorporated by reference. The plugs are rectangular with tapered front ends and tool receiving rear ends. Generally, the plugs may be used in a similar manner to the spinal screws of Michelson. As with the spinal screws, the plugs may be inserted between adjacent vertebrae. The plugs may include nubs that behave like teeth, countering any tendency for the plugs to slip between the vertebrae.

While the related art teaches various forms of spinal fusion implants, there are many shortcomings. Related art prostheses lack selectively applied bone growth promoting treatments. The prior art does not teach the selective application of the variety of known bone growth promoting treatments. There is therefore a need in the art for prostheses that incorporate selectively applied bone growth promoting treatments.

SUMMARY OF THE INVENTION

A spinal fixation system including a bone growth promoting agent is disclosed. In one aspect, the invention provides a spinal fixation system, comprising: a screw configured for implantation into at least one vertebral body; the screw including a screw body; a rod that is coupled to the screw using a coupling device, the rod including a first region and a second region; and where a bone growth promoting agent is selectively applied to the first region of the rod.

In another aspect, the rod is associated with two or more screws, each screw including a screw body with a bone growth promoting agent selectively applied to the screw body.

In another aspect, the coupling device includes a bone growth promoting agent.

In another aspect, the entire outer surface of the rod includes a bone growth promoting agent.

In another aspect, the rod is associated with multiple hooks and multiple connecting devices for fixing the hooks to the rod, and wherein the multiple hooks include a selectively applied bone growth promoting agent.

In another aspect, the invention provides a spinal fixation system, comprising: a first screw configured for implantation into a set of cervical vertebrae and a second screw configured for implantation into a first portion of the skull; the first screw and the second screw each including a first screw body and a second screw body; a rod that is coupled to the first screw and the second screw using a first coupling device and a second coupling device, the rod including a first region and a second region; and where a bone growth promoting agent is selectively applied to the first region of the rod and the first and second screw bodies.

In another aspect, the first screw is associated with a first screw set that is configured for implantation into the first portion of the skull.

In another aspect, the second screw is associated with a second screw set that is configured for implantation into the set of vertebrae within the spine.

In another aspect, the entirety of the rod includes a bone growth promoting agent.

In another aspect, the screws comprising the first screw set include screw bodies with a selectively applied bone growth promoting agent.

In another aspect, the screws comprising the second screw set include screw bodies with a selectively applied bone growth promoting agent.

In another aspect, the first coupling device and the second coupling device include a bone growth promoting agent.

In another aspect, the invention provides a spinal fixation system, comprising: a plate associated with a set of vertebrae, including a first side and a second side; the plate including at least one hole configured to receive at least one screw; and where a bone growth promoting agent is selectively applied to the first side of the plate.

In another aspect, the bone growth promoting agent is selectively applied to the entirety of the first side of the plate.

In another aspect, the first side includes a first region, and wherein a bone growth promoting agent is selectively applied to the first region.

In another aspect, the plate is associated with an anterior side of the set of vertebrae.

In another aspect, the plate is associated with a lateral side of the set of vertebrae.

In another aspect, the plate is associated with a posterior side of the set of vertebrae.

In another aspect, the invention provides a spinal fixation system, comprising: a first plate associated with a vertebral lamina; a set of screws configured to attach the first plate to the vertebral lamina; and where a bone growth promoting agent is selectively applied to the first plate.

In another aspect, the vertebral lamina is opened to widen a spinal canal.

In another aspect, the vertebral lamina includes a first end and a second end.

In another aspect, the first plate is associated with the first end and the second end.

In another aspect, new bone growth associated with the plate fuses the spinal canal closed.

In another aspect, the invention provides a spinal fixation system, comprising: a screw including a first portion and a second portion; the first portion associated with a first vertebral body; the second portion associated with a second vertebral body; and where a bone growth promoting agent is selectively applied to the screw.

In another aspect, the screw is cannulated.

In another aspect, the first vertebral body is lumbar.

In another aspect, the second vertebral body is a sacrum.

In another aspect, the second vertebral body is also lumbar.

In another aspect, the invention includes a cable including a first portion and a second portion; the first portion having a bone growth promoting agent selectively applied in a first pattern; the second portion having bone growth promoting agent selectively applied in a second pattern; where the first pattern is different than the second pattern.

In another aspect, the second pattern includes the bone growth promoting agent applied to the entire second portion.

In another aspect, the first pattern is substantially free of bone growth promoting agent.

In another aspect, the cable includes one or more strands of wire.

Other systems, methods, features and advantages of the invention will be, or will become apparent to one with skill in the art upon examination of the following figures and detailed description. It is intended that all such additional systems, methods, features and advantages be included within this description, be within the scope of the invention, and be protected by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like reference numerals designate corresponding parts throughout the different views.

FIG. 6 is an isometric view of a preferred embodiment of a rod and a sleeve;

FIG. 7 is an isometric view of a preferred embodiment of a rod with a bone growth promoting agent;

FIG. 8 is an isometric view of a preferred embodiment of a rod with a bone growth promoting agent applied along a single portion;

FIG. 9 is an isometric view of a preferred embodiment of a rod with a bone growth promoting agent applied along several portions;

FIG. 10 is an isometric view of a preferred embodiment of a rod with a bone growth promoting agent applied as a striped pattern;

FIG. 11 is an isometric view of a preferred embodiment of a rod with a bone growth promoting agent applied as a spotted pattern;

FIG. 12 is an isometric view of a preferred embodiment of a rod with a bone growth promoting agent applied as a geometric pattern;

FIG. 13 is an isometric view of a preferred embodiment of a rod with a bone growth promoting agent applied as a spiral pattern;

FIG. 23 is an isometric view of a preferred embodiment of a rod with various bone growth promoting agents;

FIG. 24 is an isometric view of a preferred embodiment of a solid rod;

FIG. 25 is an isometric view of a preferred embodiment of a hollow rod;

FIG. 26 is an isometric view of a preferred embodiment of a solid rod with holes;

FIG. 27 is an isometric view of a preferred embodiment of a hollow rod with holes;

FIG. 28 is a schematic cross sectional view of a preferred embodiment of a hollow rod with holes;

DETAILED DESCRIPTION OF THE PREFERRED EMBODIMENTS

Figure 1:
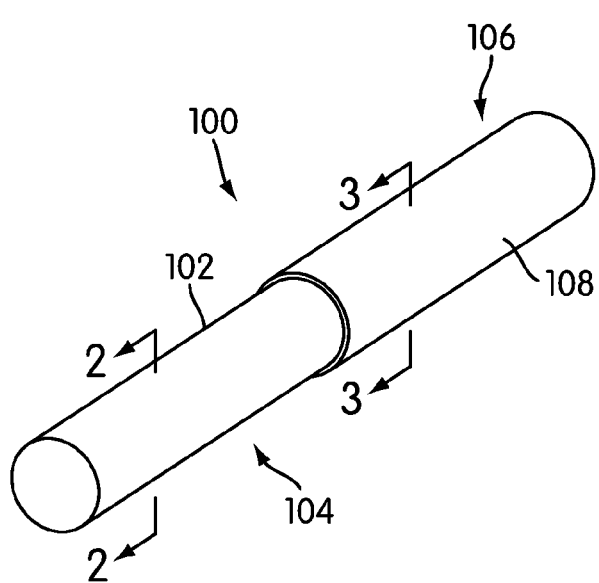
FIG. 1 is an isometric view of a preferred embodiment of a rod.

FIG. 1 is a preferred embodiment of an implantable prosthesis in the form of rod 100. For clarity, the following detailed description discusses a preferred embodiment, however, it should be kept in mind that the present invention could also take the form of any other kind of implantable prosthesis including, for example, screws, fracture plates, cages, connectors, wires, cables, clamps, staples, anchors or any other kind of prosthesis.

Often, an implantable prosthesis may include a provision for promoting bone growth. Generally, throughout this specification and the claims, such a provision will be referred to as a bone growth promoting agent. Bone growth promoting agents may be divided into two categories. The first category includes any provision that uses additive components to the prosthesis itself. The second category includes any provision that modifies the surface structure of the prosthesis, which is often metallic.

The first category may include provisions that are freeze dried onto a surface or adhered to the metal through the use of linker molecules or a binder. Examples of the first category that may be applied through these techniques include, but are not limited to, bone morphogenetic proteins (BMPs), such as BMP-1, BMP-2, BMP-4, BMP-6, and BMP-7. These are hormones that convert stem cells into bone forming cells. Further examples include recombinant human BMPs (rhBMPs), such as rhBMP-2, rhBMP-4, and rhBMP-7. Still further examples include platelet derived growth factor (PDGF), fibroblast growth factor (FGF), collagen, BMP mimetic peptides, as well as RGD peptides. Generally, combinations of these chemicals may also be used. These chemicals can be applied using a sponge, matrix or gel.

Some chemicals from the first category may also be applied to an implantable prosthesis through the use of a plasma spray or electrochemical techniques. Examples of these chemicals include, but are not limited to, hydroxyapatite, beta tri-calcium phosphate, calcium sulfate, calcium carbonate, as well as other chemicals.

Provisions from the second category generally modify the surface structure of the prosthesis. In some cases, the surface structure is roughened or provided with irregularities. Generally, this roughened structure may be accomplished through the use of acid etching, bead or grit blasting, sputter coating with titanium, sintering beads of titanium or cobalt chrome onto the implant surface, as well as other methods. This can result in a prosthesis with a surface roughness with about 3-5 microns of roughness peak to valley. However, in some embodiments, the surface roughness may be less than 3-5 microns peak to valley, and in other embodiments, the surface roughness may be greater than 3-5 microns peak to valley. In some exemplary embodiments, the prosthesis can be made of commercially pure titanium or a titanium alloy (such as Ti6Al4V) with about 3-5 microns of roughness peak to valley.

It should be understood that the provisions listed here are not meant to be an exhaustive list of possible bone growth promoting agents. The term bone growth promoting agent, as used in this specification and claims, is intended to include any method of modifying an implantable prosthesis that stimulates bone growth either directly or indirectly.

Rod 100 preferably includes outer surface 102. In some embodiments, outer surface 102 preferably includes first portion 104 and second portion 106. In this embodiment, coating 108 has been applied to second portion 106 of outer surface 102. In a preferred embodiment, coating 108 includes a bone growth promoting agent of some kind.

Figure 2:
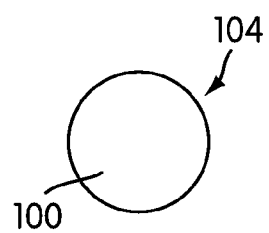
FIG. 2 is a cross sectional view of a preferred embodiment of a rod.
Figure 3:
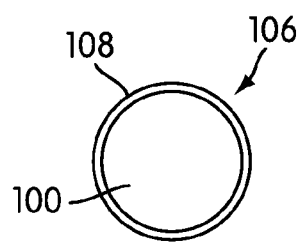
FIG. 3 is a cross sectional view of a preferred embodiment of a rod.

Referring to FIGS. 2-3, cross sections of first portion 104 and second portion 106 preferably differ. In particular, second portion 106 preferably includes coating 108. In this embodiment, coating 108 preferably has some thickness. In other embodiments, the thickness of coating 108 may be varied.

As previously mentioned, bone growth promoting agents may be applied in a variety of ways. In some embodiments, bone growth promoting agents may be applied to a mesh or fabric material that may be independently manufactured from the implantable prosthesis. In this manner, the fabric or mesh material, which includes the bone growth promoting agent, may be applied to the implantable prosthesis at any time prior to surgery, during surgery or even after implantation. In addition to mesh or a fabric material, the sheet can be any kind of bio-compatible material that includes a metallic foil, a plastic sheet or a biological matrix. The metal can be titanium, stainless steel, cobalt chrome or any other type of bio-compatible metal or matrix.

Figure 4:
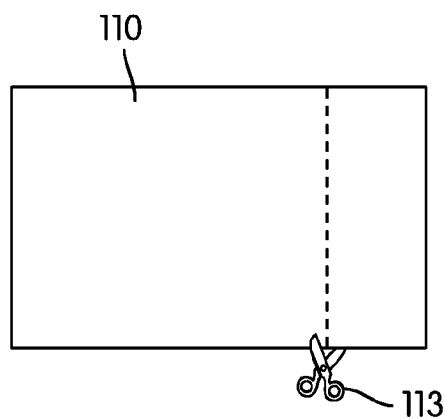
FIG. 4 is a plan view of a preferred embodiment of a sheet material.
Figure 5:
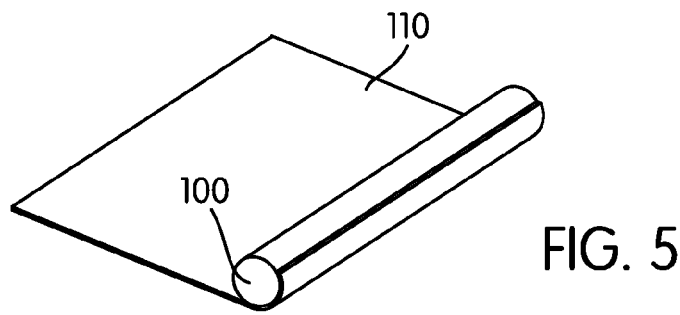
FIG. 5 is an isometric view of a preferred embodiment of a sheet material being applied to a rod.

Referring to FIGS. 4-5, sheet material 110 may be constructed to include a bone growth promoting agent. In some embodiments, sheet material 110 may be any material that may be configured to include a bone growth promoting agent, and that is flexible enough to wrap around an implantable prosthesis. In a preferred embodiment, sheet material 110 may be a mesh or continuous fabric. In this embodiment, scissors 113 may be used to cut sheet material 110 to a preconfigured size, which can be any desired size.

Once sheet material 110 has been cut to an appropriate size, it may be applied to rod 100. Generally, sheet material 110 may be rolled over rod 100. In some embodiments, sheet material 110 may be attached to rod 100 through an adhesive. It is also possible to attach sheet material 110 to rod 100 by using mechanical provisions, including hooks, microscopic hooks, temperature difference, interference fit or a Morris taper. It is also possible to attach sheet material 110 to rod 100 using magnetic features. In a preferred embodiment, sheet material 110 may be preconfigured to include an adhesive for attaching to rod 100.

In some embodiments, a sheet material may be preconfigured as a sleeve or any desired shape. Preferably, the sleeve may be configured so that a rod or another type of prosthesis may be inserted into the sleeve, without the need to wrap the sheet material around the prosthesis. The sleeve can come in a variety of sizes and shapes. Like the sheet material, the sleeve material may be constructed of a continuous or mesh fabric, collagen, or biologic matrix, metallic foil or plastic sheet.

Referring to FIG. 6, sleeve material 112 may be constructed to include a bone growth promoting agent. Preferably, sleeve material 112 may be configured to receive all or a portion of a rod 100. Generally, sleeve material 112 may be configured to receive all or a portion of an implantable prosthesis. In this manner, a bone growth promoting agent may be applied via sleeve material 112 by simply inserting the prosthesis into sleeve material 112. This configuration allows a bone growth promoting agent to be applied to a rod in an efficient manner.

Preferably, sheet material 110 and sleeve material 112 may be applied to multiple types of implantable prosthesis, including, but not limited to screws, fracture plates, cages, connectors, wires, cables, clamps, staples, anchors or any other kind of prosthesis. In some embodiments, sheet material 110 may be cut to a size configured to cover all or a portion of an implantable prosthesis. Additionally, sleeve material 112 may be constructed in a manner that allows all or a portion of an implantable prosthesis to be inserted into sleeve material 112.

Preferably, a rod intended to be used as a prosthesis includes provisions for selectively applying a bone growth promoting agent to various portions of the rod. In other words, a bone growth promoting agent need not be applied to the entirety of the rod. Instead, the bone growth promoting agent may be applied to a single portion of the rod. In some embodiments, the bone growth promoting agent may be applied to multiple, but not all, portions of the rod. Additionally, the bone growth promoting agent may be applied differently along different portions of the rod. In this manner, the rod may be used to differentially stimulate bone growth along various portions of the adjacent bone to simulate fusion, healing, stabilization and/or incorporation. This may be useful in cases where some, but not all, portions of the bone are damaged.

Referring to FIGS. 7-9, several embodiments of a rod may include a bone growth promoting agent that has been applied along various portions. For the purposes of illustration, the thicknesses of the portions including a bone growth promoting agent have been exaggerated. Generally, these thicknesses may vary. Some bone growth promoting agents may be applied to the surface of a rod, or other prosthesis, and have no visible thickness.

In some embodiments, the bone growth promoting agent may be applied to the entirety of the rod. Rod 120 preferably includes bone growth promoting agent 122 along the entirety of the length of rod 120. Bone growth promoting agent 122 may be any of the possible provisions discussed previously for applying a bone growth promoting agent to an implantable prosthesis. With this configuration, rod 120 may help to stimulate bone growth along the entirety its length, following the implantation of rod 120.

In other embodiments, a rod may include three portions, with only one portion including a bone growth promoting agent. Rod 124 preferably includes first portion 126, second portion 128, and third portion 130. In a preferred embodiment, second portion 128 includes bone growth promoting agent 132. With this configuration, rod 124 may help to stimulate bone growth along a portion of the bone adjacent to second portion 128, following the implantation of rod 124.

In another embodiment, a rod may include four portions, with alternating portions including a bone growth promoting agent. Preferably, rod 134 may include first portion 136, second portion 138, third portion 140, and fourth portion 142. In some embodiments, only first portion 136 and third portion 140 include bone growth promoting agent 144. With this configuration, rod 134 may help to stimulate bone growth along portions of the bone adjacent to first portion 136 and third portion 140, following the implantation of rod 134. In other embodiments, more or less than four portions may be provided.

In the previous embodiments, along portions where a bone growth promoting agent has been applied, it has been preferably applied uniformly throughout the portion. In some embodiments, however, a bone growth promoting agent may be applied in particular patterns throughout a portion. Depending on the circumstances, different types of patterns may be used to promote bone growth.

Examples of some patterns include stripes, spots, helical or spiral, geometric patterns, or combinations incorporating one or more of these basic pattern elements. The term geometric pattern refers to any polygonal pattern including square (shown in the Figures), rectangular, polygon, honeycomb, repeating, non-repeating, regular, irregular, as well as other types of patterns. A striped pattern includes thin lines of bone growth promoting agent that are disposed along a particular portion. In this arrangement, there is no bone growth promoting agent between the stripes. A spotted pattern may include small spots of the bone growth promoting agent. In a similar manner, a geometric pattern may include alternating shapes of a bone growth promoting agent. Various patterns may be used depending on the way in which the user wants to induce bone growth along or adjacent to the prosthetic.

FIGS. 10-13 illustrate various patterns of bone growth promoting agents applied to rods. Rod 150 preferably includes first portion 152. In some embodiments, first portion 152 may include bone growth promoting agent 154. In a preferred embodiment, bone growth promoting agent 154 may be disposed in a striped pattern as shown in FIG. 10. This striped pattern may include one or more stripes. Generally, the thickness and/or density of these stripes may be varied. Additionally, their orientation may also be varied. The shape, density and/or distribution of the bone growth promoting agent will allow for selectively tailored bone growth or fusion.

In a second embodiment, rod 156 preferably includes first portion 158. In some embodiments, first portion 158 may include bone growth promoting agent 160. In a preferred embodiment, bone growth promoting agent 160 may be disposed in spots along first portion 158. Generally, the shape and/or density of these spots may be varied.

In a third embodiment, rod 162 preferably includes first portion 164. In some embodiments, first portion 164 may include bone growth promoting agent 166. In a preferred embodiment, bone growth promoting agent 166 may be disposed in a geometric pattern along first portion 164. Generally, the size of the squares comprising this geometric pattern may be varied.

In a fourth embodiment, rod 170 preferably includes first portion 172. In some embodiments, first portion 172 may include bone growth promoting agent 174. In a preferred embodiment, bone growth promoting agent 174 may be disposed in a spiral or helical pattern along first portion 172. Generally, the thickness and spacing of this spiral pattern may be varied.

The patterns disclosed here are not intended to be exhaustive, but only illustrative of the various types of patterns that may be included in portions where a bone growth promoting agent is applied to a rod or other implantable prosthesis. Generally, any type of pattern may be used. Additionally, within the same portion, multiple patterns may be superimposed.

Figure 14:
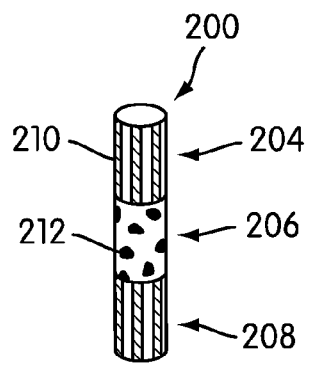
FIG. 14 is an isometric view of a preferred embodiment of a rod with a bone growth promoting agent applied as various patterns.
Figure 15:
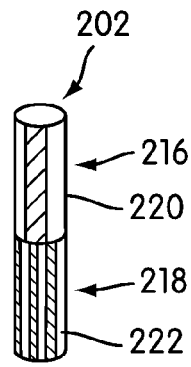
FIG. 15 is an isometric view of a preferred embodiment of a rod with a bone growth promoting agent applied as various patterns.
Figure 16:
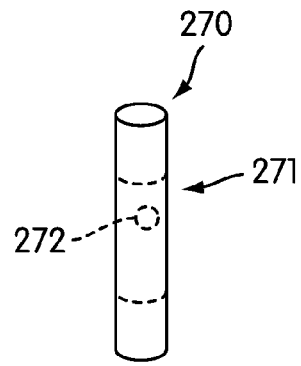
FIG. 16 is an isometric view of a preferred embodiment of a rod with a modified surface texture.
Figure 17:
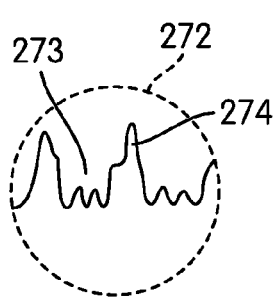
FIG. 17 is a side view of a preferred embodiment of a microscopic surface texture.
Figure 18:
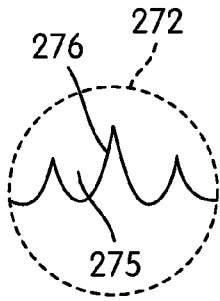
FIG. 18 is a side view of a preferred embodiment of a microscopic surface texture.
Figure 19:
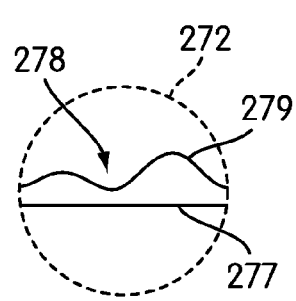
FIG. 19 is a side view of a preferred embodiment of a microscopic surface texture.

Generally, various patterns of bone growth promoting agents may be selectively applied to multiple portions of a rod or other implantable prostheses. FIGS. 14-15 are a preferred embodiment of first rod 200 and second rod 202. In some embodiments, first rod 200 includes first portion 204, second portion 206, and third portion 208. In some embodiments, a distinct pattern of a bone growth promoting agent may be selectively applied to each of the portions 204, 206, and 208. In a preferred embodiment, first portion 204 and third portion 208 may include bone growth promoting agent 210 arranged as stripes. Likewise, second portion 206 may include bone growth promoting agent 212 arranged as spots.

Preferably, second rod 202 includes first portion 216 and second portion 218. In some embodiments, both first portion 216 and second portion 218 include the same pattern of a bone growth promoting agent. In some embodiments, both portions 216 and 218 include a bone growth promoting agent arranged as stripes. In some embodiments, first portion 216 includes first striped pattern 220 of a bone growth promoting agent, while second portion 218 includes second striped pattern 222 of a bone growth promoting agent. In a preferred embodiment, the density of first striped pattern 220 is lower than the density of second striped pattern 222. First striped pattern 220 can have different a orientation and can be angled with respect to second striped pattern 222.

Referring to FIGS. 16-22, bone growth promoting agents may also be selectively applied to various portions of a rod by modification of the surface properties. Preferably, rod 270 includes first portion 271. In some embodiments, first portion 271 may include a bone growth promoting agent in the form of a textured surface. The structure of this surface may be seen in a close up of patch 272.

In some embodiments, first portion 271 may include a textured surface due to acid etching of titanium. In this case, a side view of patch 272, when viewed at the microscopic level, may include jagged peaks 274 and jagged valleys 273. In another embodiment, first portion 271 may include a textured surface due to grit blasting the titanium. In this case, a side view of patch 272, when viewed at a microscopic level, may include sharp peaks 276 and smooth valleys 275. Finally, in an embodiment where plasma spraying is used to texture the surface of portion 271, a side view of patch 272 may include rounded peaks 279, rounded valleys 278, and under surface 277.

Figure 20:
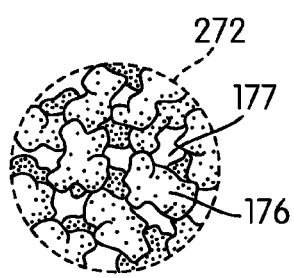
FIG. 20 is a top down view of a preferred embodiment of a three dimensional surface texture.
Figure 21:
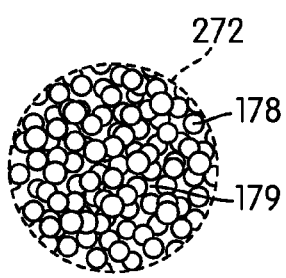
FIG. 21 is a top down view of a preferred embodiment of a three dimensional surface texture.
Figure 22:
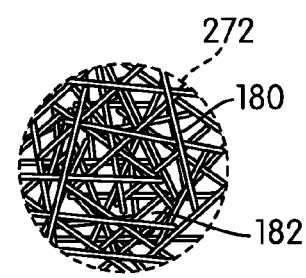
FIG. 22 is a top down view of a preferred embodiment of a three dimensional surface texture.

Referring to FIGS. 20-22, some rods may be configured so that the surface includes various three dimensional structures. In some embodiments, first surface 272 may include an irregular three dimensional surface. FIG. 20 shows an embodiment including an irregular porous titanium construct, including irregular structures 176 and first pores 177. In a preferred embodiment, the sizes of first pores 177 may be between 100 and 600 microns. In another embodiment, first surface 272 may include a regular three dimensional surface. FIG. 21 shows an embodiment including a regular ball bearing type structure made of titanium, including ball bearing-like structures 178 and second pores 179. Second pores 179 may also have a size between 100 and 600 microns. In another embodiment, shown in FIG. 22, first surface 272 may include a fibrous three dimensional surface. In this embodiment, the fibrous surface includes fibrous structures 180 and third pores 182. Using these various types of three dimensional structures on the surface of rod 270 allows for an increased surface area for new bone growth, as opposed to traditional surface treatment methods. In particular, the height or thickness of these various surface treatments may be large when compared with traditional surface treatments.

Other surface treatments that can be used include microporous coatings. Additionally, any and all coatings, treatments or patterns can be used that promote bone growth or allow for bone growth to the prosthesis and effectively lock the prosthesis to the bone. In some embodiments, these surface treatments can provide the surface of the prosthesis with a roughness of about 3-5 microns, peak to valley, or a pore size of about 1-850 microns as previously discussed. The pore size can be increased if desired. However, in other embodiments, the peak to valley roughness will be greater than 3-5 microns, and in other embodiments, the peak to valley roughness may be less than 3-5 microns, depending on the application. In some cases, these surface treatments will be invisible to the naked eye.

The specific surface treatment feature or combination of features can be selected based on: biology, location, bony region (metaphyseal or cortical bone; weight bearing or non-weight bearing, for example) cost, strength of the implant or prosthesis, geometry or size of the implant or prosthesis and manufacturing feasibility, among other criteria or factors that may be considered.

In some embodiments, a rod may include a chemical bone growth promoting agent along one portion and a modified surface bone growth promoting agent along a second portion. In a preferred embodiment, shown in FIG. 23, rod 282 may include first region 280 and second region 281. In some embodiments, each of the regions 280 and 281 may include a different bone growth promoting agent. In a preferred embodiment, first region 280 may include striped pattern 284 of a chemical bone growth promoting agent. Also, second region 281 may include acid etched surface 285, another type of bone growth promoting agent. For the purposes of illustration, acid etched surface 285 is shown here with some shading, but generally, textured surfaces may be invisible to the naked eye.

Generally, some rods include provisions for modifying the structure of the rod. These modifications may include a hollowing out of the core of the rod. Additionally, these modifications may include the addition of holes that may be disposed along the outer surface of the rod and penetrate into the core of the rod.

Referring to FIGS. 24-27, rods may be configured solid, hollow, and with or without holes. If the rod includes holes, the holes can be any desired size and shape. Also, the distribution pattern of the holes may be varied. In one embodiment, a section of rod 230 may be solid. Rod 230 may include outer surface 232. In a preferred embodiment, core 234 of rod 230 may be solid. In a second embodiment, a section of rod 236 may include hollow central core 238. Preferably, rod 236 includes outer surface 240. In a preferred embodiment, rod 236 may also include inner surface 242 of hollow central core 238.

Preferably, a third embodiment of a section of rod 244 may include holes 246. Holes 246 are preferably disposed along the entirety of rod 244 along outer surface 247. Holes 246 may also be disposed along a single portion of rod 244 in other embodiments. Generally, holes 246 may be any depth, any shape, angle, and have any size circumference. Similarly, the density of holes 246 may be varied in other embodiments. In some embodiments, a combination of holes having different sizes, shapes, angles or densities may be used.

A fourth embodiment of a section of rod 248 may preferably include hollow central core 250 as well as holes 252. Holes 252 are preferably disposed along the entirety of rod 248. Generally, holes 252 may be any depth, any shape, angle, and have any size circumference. Similarly, the density of holes 252 may be varied in other embodiments. In some embodiments, a combination of holes having different sizes, shapes, angles or densities may be used. Holes 252 may or may not penetrate through to hollow central core 250. In a preferred embodiment, holes 252 are disposed between outer surface 254 and inner surface 256 of hollow central core 250. In this manner, holes 252 preferably allow fluid communication between hollow central core 250 and outer surface 254, which allows bony ingrowth to occur into the interstices of rod 248.

Preferably, an implantable prosthesis system may include provisions for fusing the prosthesis to the bone. In some embodiments, a rod may be configured to be fused to a bone once it has been implanted. In particular, the rod may include provisions that allow the bone to penetrate through the outer surface and grow along an inner surface of a hollow core or into the holes themselves, and into the bone growth promoting agent of the prosthesis.

In some embodiments, outer surface 254 may include bone growth promoting agent 258, seen in FIG. 28, a cross sectional view of rod 248. In some embodiments, inner surface 256 may also include bone growth promoting agent 258. Additionally, holes 252 may also be lined with bone growth promoting agent 258. This configuration preferably allows bone to grow along outer surface 254 as well as inner surface 256, via holes 252. Bone growth can also occur into the holes themselves, and into the bone growth promoting agent of the prosthesis.

Figure 29:
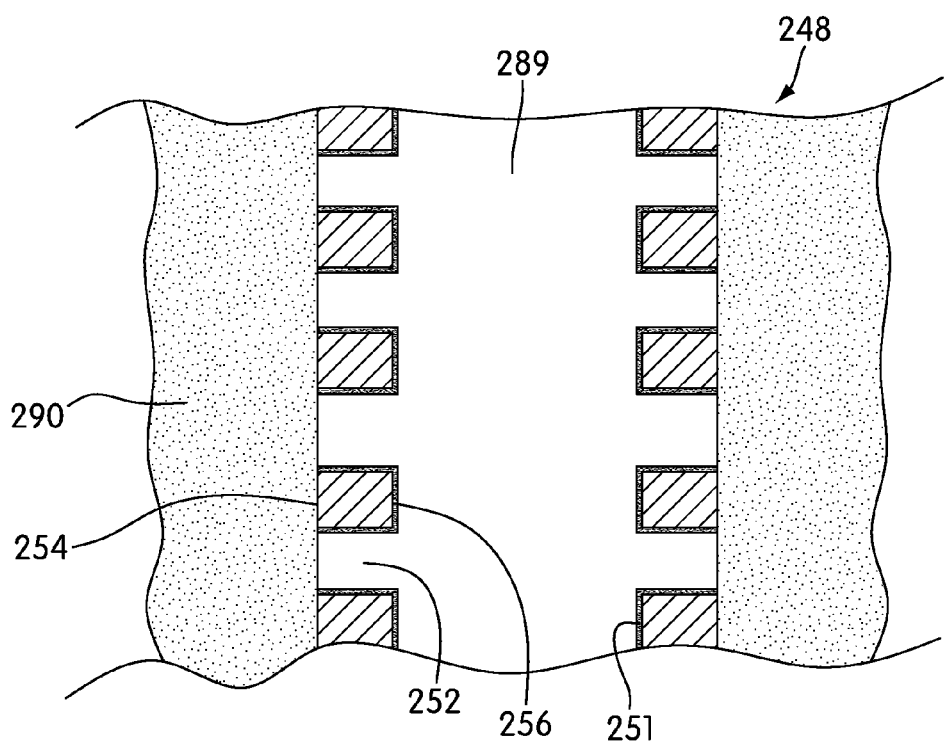
FIG. 29 is a schematic cross sectional view of a preferred embodiment of a rod inserted into bone.
Figure 30:
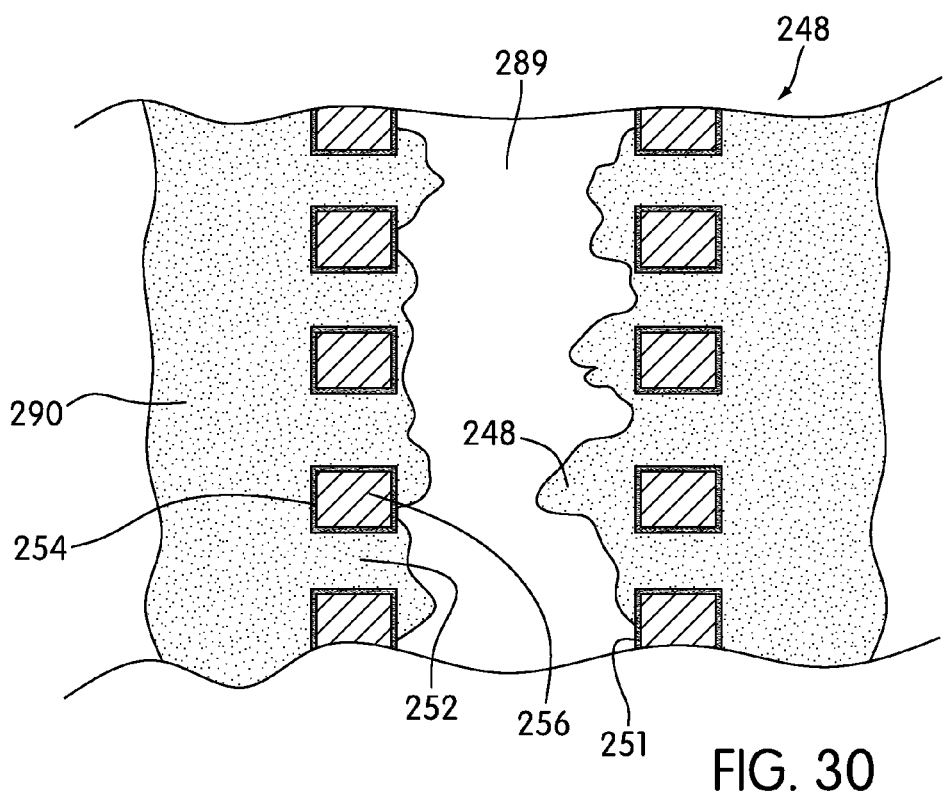
FIG. 30 is a schematic cross sectional view of a preferred embodiment bone growing into a rod.
Figure 31:
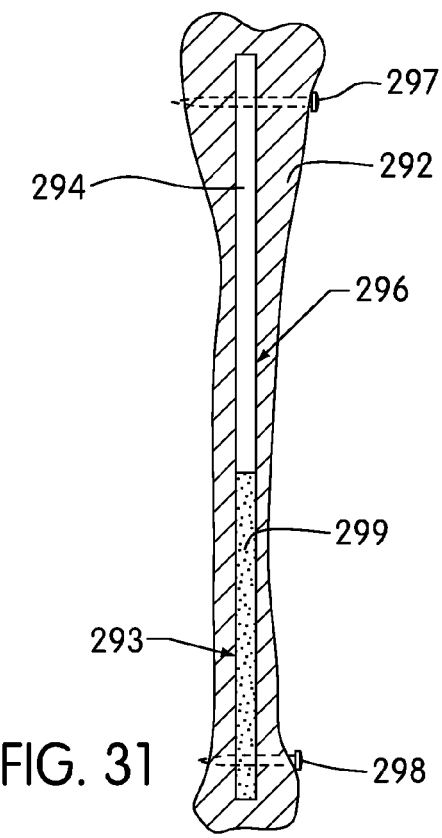
FIG. 31 is a cross sectional view of a preferred embodiment of an implantable prosthesis system.

Referring to FIGS. 29-30, ingrowth of the bone from outer surface 254 to inner surface 256 may proceed once rod 248 has been inserted into a section of bone 290 or surrounded by bone 290, whether from a fracture or fusion. With time, portions 291 of bone 290 may grow through holes 252 into hollow central core 289. In some embodiments, portions 291 may fuse together inside hollow central core 289. In this way, rod 248 may be fused with bone 290. In a preferred embodiment, holes 252 are used in conjunction with bone growth promoting agent 251 disposed along inner surface 256 and outer surface 254 in order to induce bone growth. In some embodiments, bone growth promoting agent 251 may also be disposed within holes 252. In this manner, rod 248 may be partially or fully integrated into bone 290 as it heals.

Generally, in the rod embodiment disclosed above, or in any of the embodiments disclosed below, a combination of macroscopic holes and microscopic holes or other bone growth promoting surface treatments can be used. By using a combination of both features, bone growth can be encouraged at the surface of the prosthesis so that the prosthesis, on a surface level, integrates with the bone; and by using macroscopic holes, large scale or bulk integration of the prosthesis can occur, further solidifying the integration of the prosthesis with the bone.

FIG. 28 is a cross sectional view of a preferred embodiment of implantable prosthesis system 296. Preferably, implantable prosthesis system 296 is integrated into bone 292 (seen here in cross section). Preferably, implantable prosthesis system 296 may include rod 294, as well as first bone screw 297 and second bond screw 298. In some embodiments, rod 294 may include bone growth promoting agent 299, disposed along a first portion 293 of rod 294. First portion 293 can range from a relatively small portion of rod 294 to substantially all of rod 294. In some embodiments, second screw 298 may also be coated with bone growth promoting agent 299. Generally, any desired number of screws in system 296 can include bone growth promoting agents. It is also possible that the location of various, differently treated screws is varied depending on the type of bone. For example, a screw for use in cortical bone may have one type of bone growth promoting agent, while a screw for use in cancellous or spongy bone has a second type of bone growth promoting agent. In this manner, the portion of bone 292 disposed adjacent to first portion 293 of rod 294 and second screw 298 may be stimulated to grow and fuse around rod 294 and second screw 298.

In an alternative embodiment, the implantable prosthesis may take the form of a fracture plate. In a manner similar to the rods discussed in the previous embodiments, a bone growth promoting agent may be applied to a fracture plate to stimulate bone growth. In a preferred embodiment, a bone growth promoting agent may be selectively applied to various portions of a fracture plate, stimulating bone growth along various portions of the bone.

Figure 32:
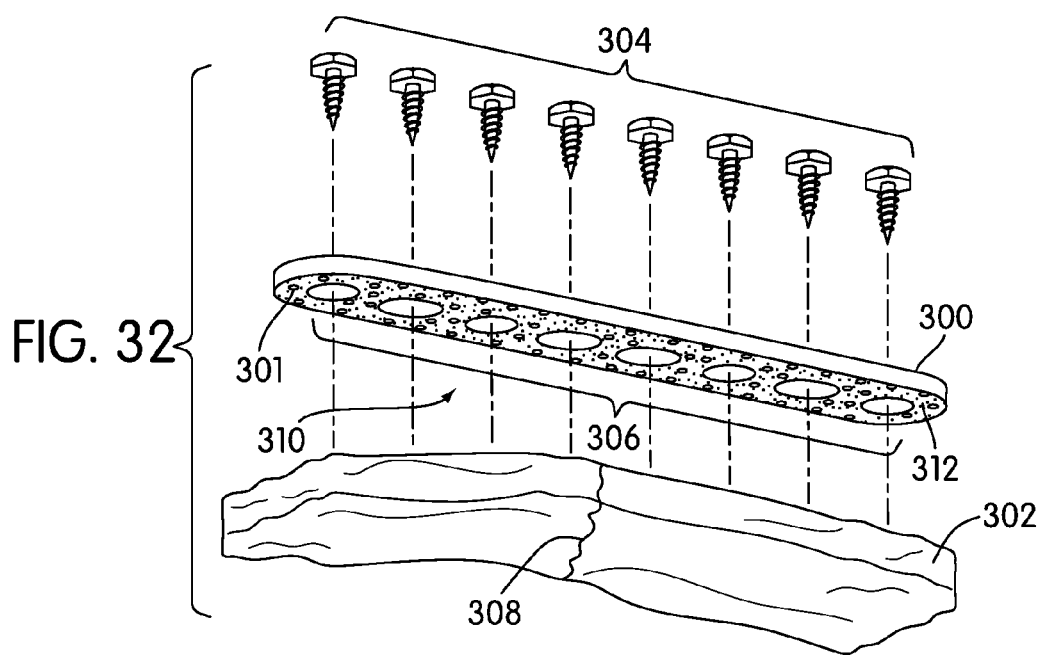
FIG. 32 is an isometric view of a preferred embodiment of a fracture plate configured to attach to a bone.
Figure 33:
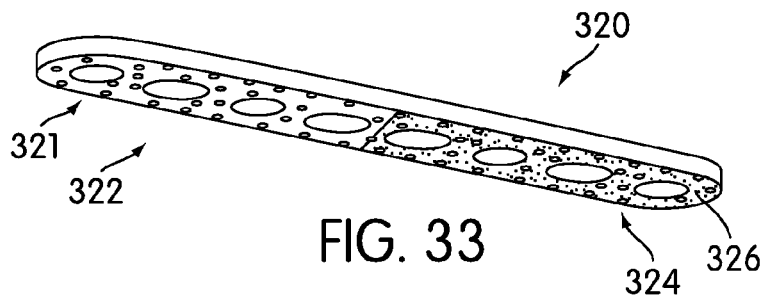
FIG. 33 is an isometric view of a preferred embodiment of a fracture plate with a bone growth promoting agent.
Figure 34:
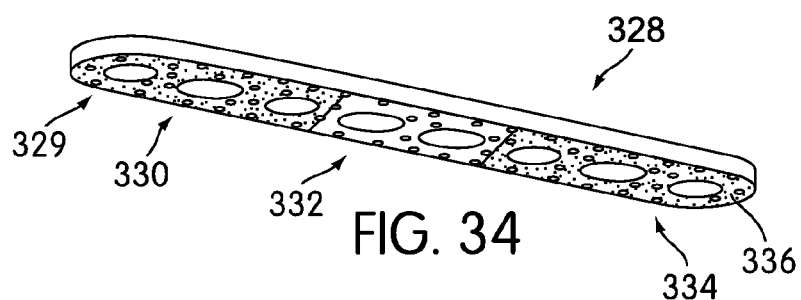
FIG. 34 is an isometric view of a preferred embodiment of a fracture plate with a bone growth promoting agent.
Figure 35:
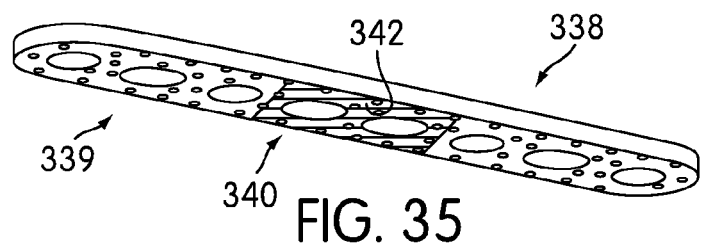
FIG. 35 is an isometric view of a preferred embodiment of a fracture plate with a bone growth promoting agent.
Figure 36:
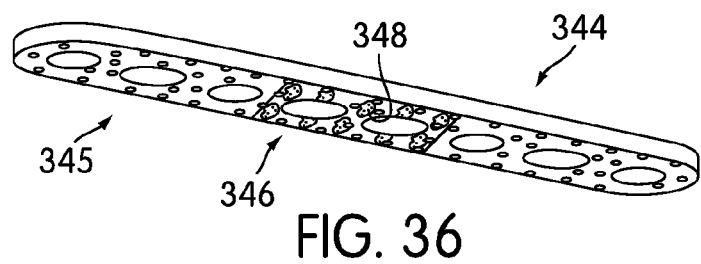
FIG. 36 is an isometric view of a preferred embodiment of a fracture plate with a bone growth promoting agent.
Figure 37:
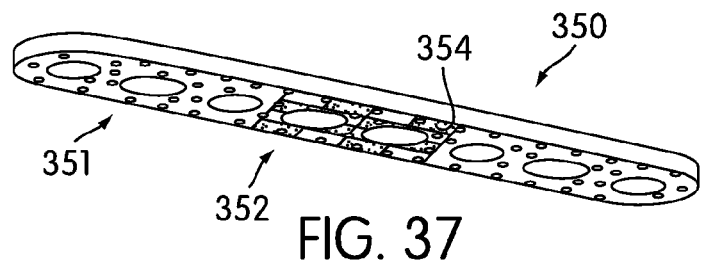
FIG. 37 is an isometric view of a preferred embodiment of a fracture plate with a bone growth promoting agent.
Figure 38:
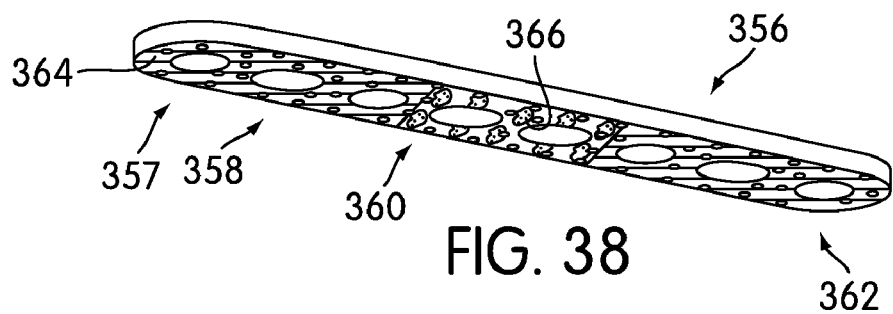
FIG. 38 is an isometric view of a preferred embodiment of a fracture plate with a bone growth promoting agent.
Figure 39:
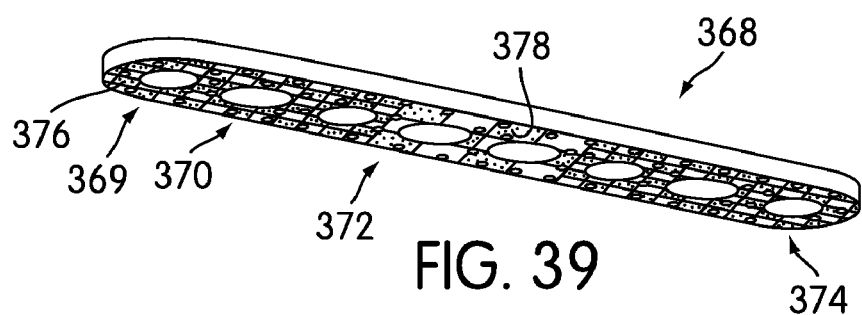
FIG. 39 is an isometric view of a preferred embodiment of a fracture plate with a bone growth promoting agent.

FIG. 32 is an exploded isometric view of a preferred embodiment of fracture plate 300 that may be attached to bone 302. Generally, fracture plate 300 may be attached to bone 302 using screw set 304. The screws comprising screw set 304 may be inserted through screw hole set 306 of fracture plate 300. With this arrangement, fracture plate 300 may be attached to bone 302 in order to add support to bone 302 while fracture 308 heals. Generally, any number of screws and screw holes may be used. In this exemplary embodiment, there are eight screws comprising screw set 304 and eight screw holes comprising screw hole set 306.

In the preferred embodiments, the profile of fracture plate 300 is minimized by the long and narrow shape of fracture plate 300. Additionally, the profile may be minimized by the use of large screw holes. This reduction in profile may decrease the tendency of fracture plate 300 to interfere with the surrounding tissue and may also help decrease the weight of fracture plate 300 while maintaining a high density for strength and durability.

In the preferred embodiment, fracture plate 300 may also include small holes 301 that are disposed on lower surface 310. Small holes 301 may be macro and/or micro holes. Small holes 301 may extend partially into fracture plate 300, or may extend all the way through. Also, small holes 301 may be disposed anywhere on lower surface 310, in any pattern, including a random pattern. The use of small holes 301 preferably facilitates both macro and micro fixation of bone growth.

In some embodiments, fracture plate 300 may include a lower surface 310. In some embodiments, lower surface 310 may be coated with bone growth promoting agent 312. Preferably, in this embodiment, bone growth promoting agent 312 may cover the entirety of lower surface 310. Generally, bone growth promoting agent 312 may be any of the types of bone growth promoting agents discussed previously.

In some embodiments, an intermediate tissue or membrane is disposed between fracture plate 300 and bone 302. In other words, fracture plate 300 may not directly contact bone 302. Instead, fracture plate 300 may be configured to contact some other tissue or membrane disposed adjacent to bone 302. This membrane can include muscle or periosteum.

As with the rods in the previous embodiments, bone growth promoting agents may be selectively applied to various portions of fracture plates. In this way, different portions of a bone in contact with a fracture plate may be stimulated to grow differently. Generally, a bone growth promoting agent may be applied to any portion of a fracture plate. Additionally, a bone growth promoting agent may be disposed in any pattern along the fracture plate. This may be useful in cases where some, but not all, portions of the bone are damaged.

Referring to FIGS. 32-41, bone growth promoting agents may be applied to a fracture plate in a variety of ways. The following embodiments are intended to illustrate possible configurations of fracture plates including one or more bone growth promoting agents, however it should be understood that these embodiments are only intended to be exemplary. Many other types of bone growth promoting agents, including various patterns may be applied to one or multiple portions of a fracture plate. Additionally, throughout the following embodiments, the bone growth promoting agents may be used in combination with macro and micro holes in order to further facilitate bony fusion.

First plate 320 preferably includes first lower surface 321. In some embodiments, first lower surface 321 may include first portion 322 and second portion 324. In some embodiments, first portion 322 and second portion 324 may have different treatments. In a preferred embodiment, first portion 322 is not treated. In a preferred embodiment, second portion 324 may be treated with bone growth promoting agent 326.

As previously discussed, bone growth promoting agent 326 may include chemical treatments of the surface, or modifications to the texture of the surface of the prosthesis. Generally, the bone growth promoting agent applied to a fracture plate may be any type of bone growth promoting agent discussed in the previous embodiments involving rods, as well as any other bone growth promoting agent. In these embodiments, the bone growth promoting agents are visually distinct from the general surface to which they are applied. However, this is done purely for illustrative purposes. In some embodiments, the bone growth promoting agents may not be visible.

Second fracture plate 328 also preferably includes several portions. In some embodiments, second plate 328 may include lower surface 329. In some embodiments, second lower surface 329 may include first portion 330, second portion 332, and third portion 334. In some embodiments, first portion 330 and third portion 334 may be treated in a similar manner. In a preferred embodiment, first portion 330 and third portion 334 both include bone growth promoting agent 336. In this manner, second fracture plate 328 preferably helps to induce growth along portions of the bone adjacent to first portion 330 and third portion 334, but not second portion 332.

Additionally, fracture plates may be treated with a bone growth promoting agent that is disposed along the outer surface in a variety of designs. These designs may be similar to the designs discussed in previous embodiments, or other types of designs. In some embodiments, fracture plates may include a bone growth promoting agent applied in striped, spotted, geometric patterns, and/or combinations of two or more of these basic patterns.

Third fracture plate 338 preferably includes center portion 340 disposed along lower surface 339. In some embodiments, center portion 340 may include a bone growth promoting agent. In a preferred embodiment, center portion 340 includes bone growth promoting agent 342 configured in a striped pattern.

In another embodiment, fourth fracture plate 344 also preferably includes center portion 346 disposed along lower surface 345. In some embodiments, center portion 346 may include a bone growth promoting agent. In a preferred embodiment, center portion 346 may include bone growth promoting agent 348 configured in a spotted pattern.

In another embodiment, fifth fracture plate 350 also preferably includes center portion 352 disposed along lower surface 351. In some embodiments, center portion 352 may include a bone growth promoting agent. In a preferred embodiment, center portion 352 preferably includes bone growth promoting agent 354 configured in a geometric pattern.

In another embodiment, sixth fracture plate 356 may include three separate portions. Preferably, sixth fracture plate 356 includes first portion 358, second portion 360, and third portion 362 disposed along lower surface 357. In some embodiments, each portion may be treated with a different bone growth promoting agent. In some embodiments, first portion 358 and third portion 362 may be treated with a similar pattern of bone growth promoting agent. In a preferred embodiment, first portion 358 and third portion 362 may include bone growth promoting agent 364 configured in a striped pattern. Also, second portion 360 may preferably include bone growth promoting agent 366 configured in a spotted pattern.

In some cases, different portions may be treated with the same pattern of bone growth promoting agents, but the size or density of the pattern may differ between portions. Seventh fracture plate 368 preferably includes several portions disposed along lower surface 369. In particular, seventh fracture plate 368 preferably includes first portion 370, second portion 372, and third portion 374. In some embodiments, each of these portions 370, 372 and 374 may include a bone growth promoting agent disposed in a geometric pattern. In a preferred embodiment, first portion 370 and third portion 374 may include a first bone growth promoting agent 376 disposed in a high density geometric pattern. Likewise, second portion 372 may include a second bone growth promoting agent 378 disposed in a low density geometric pattern.

In the previous embodiments, a bone growth promoting agent was applied along portions that were disposed along the width of the fracture plates. In some embodiments, however, the bone growth promoting agent may be disposed along portions that are oriented along the length of the fracture plates. Additionally, a fracture plate may be divided into several portions disposed along the length of the fracture plate, each portion including a different type of bone growth promoting agent.

Figure 40:
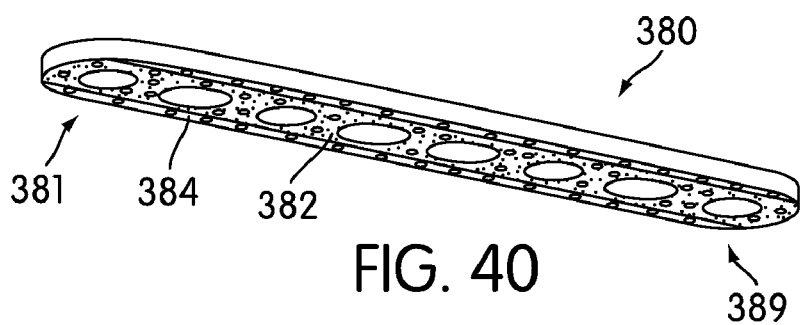
FIG. 40 is an isometric view of a preferred embodiment of a fracture plate with a bone growth promoting agent.
Figure 41:
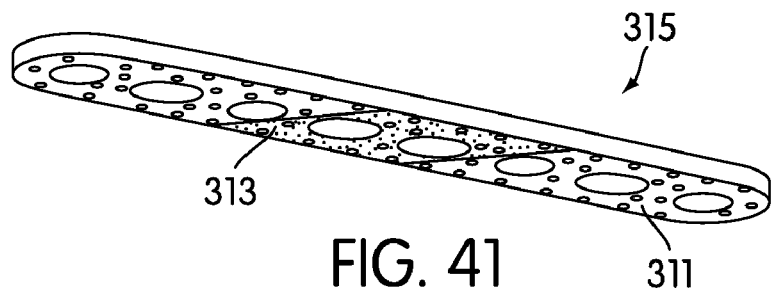
FIG. 41 is an isometric view of a preferred embodiment of a fracture plate with a bone growth promoting agent.

FIG. 40 is a preferred embodiment of fracture plate 380. In some embodiments, fracture plate 380 may include lower surface 381. In some embodiments, lower surface 381 may be coated with bone growth promoting agent 382 along vertical portion 389. FIG. 41 illustrates an embodiment of a fracture plate. In this embodiment, fracture plate 315 includes a diagonally applied bone growth promoting agent 313 onto lower surface 311. Using either a vertically or diagonally applied bone growth promoting agent may facilitate new bone growth along the length of a fracture plate.

In some embodiments, a fracture plate may include additional provisions for inducing bone growth, such as a porous surface. Additionally, fracture plate 380 may include holes 384 disposed along lower surface 381. Generally, holes 384 may have circumferences of various sizes. Likewise, holes 384 may have various depths. Holes 384 need not be disposed along the entirety of fracture plate 380. In some embodiments, holes 384 may be confined to one or multiple portions of a fracture plate. As disclosed above, fracture plate 380 is an example of a prosthesis that includes both macroscopic holes 384 and microscopic bone growth promoting features or agents 382. These macroscopic and microscopic features can be used in combination to help integrate fracture plate 380 to the bone in a macroscopic and microscopic scale.

In another embodiment, a fracture plate may include a liner. In some embodiments, the liner may fit into a recess disposed in the fracture plate. However, in other embodiments, no recess is provided for the liner. Generally, the liner may be formed of or coated with a bone growth promoting agent. The bone growth promoting agent may be disposed on the liner in any pattern, such as those patterns described above with respect to the fracture plate. In this manner, a liner with a bone growth promoting agent may be manufactured separately from the fracture plate, and combined with the fracture plate at the time of surgery, during implantation, or after implantation. It is also possible to provide a fracture plate with a pre-installed liner so there is no need for the surgeon to associate the liner with the fracture plate at the time of surgery.

In some embodiments, the liner may be attached to the fracture plate through an adhesive. It is also possible to attach the liner to the fracture plate by using mechanical provisions, including hooks, microscopic hooks, temperature difference, interference fit or a Morris taper. It is also possible to attach the liner to the fracture plate using magnetic features. In some embodiments, liner may be preconfigured to include an adhesive for attaching to the fracture plate.

Figure 42:
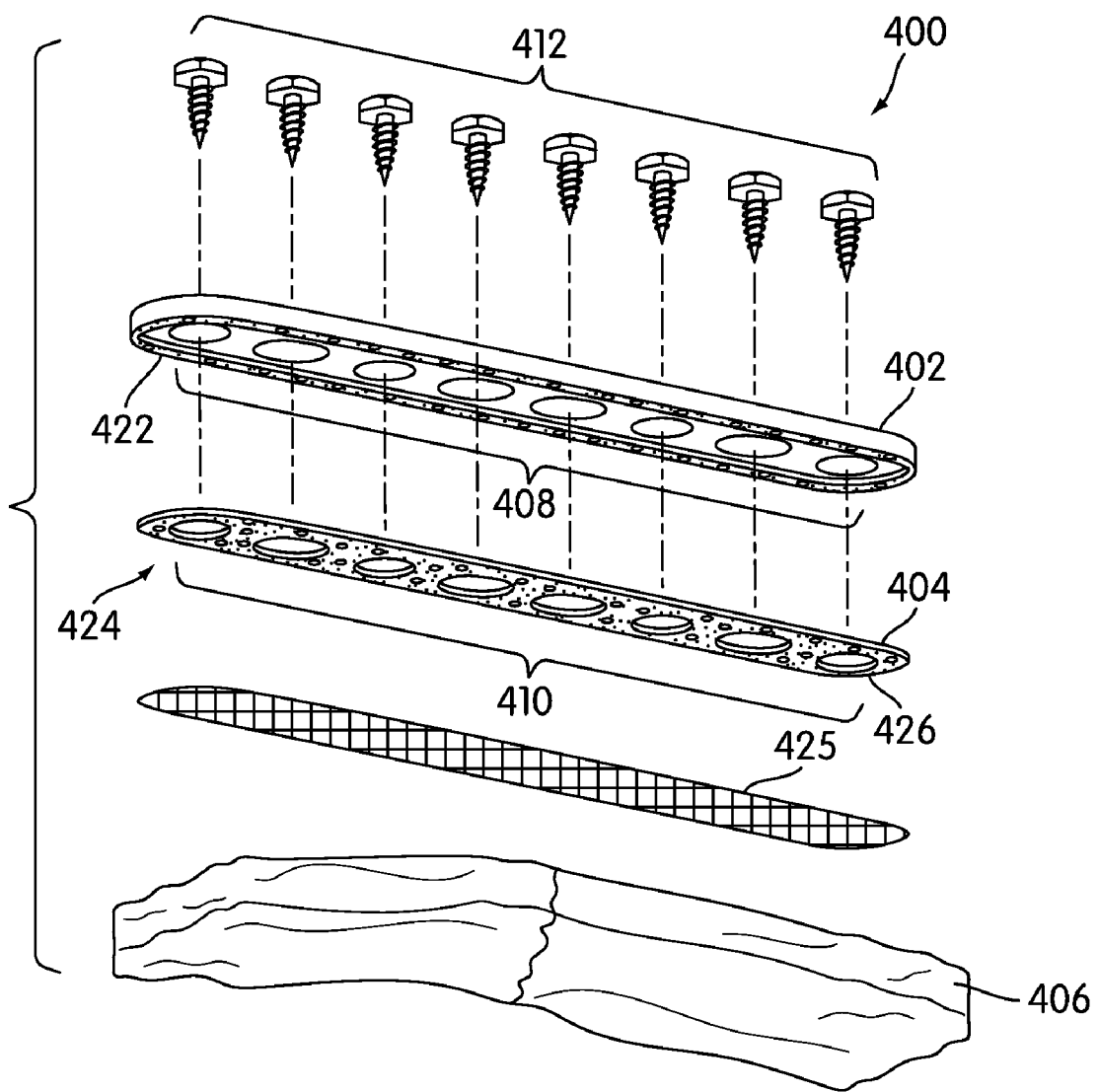
FIG. 42 is an isometric view of a preferred embodiment of a liner system.

FIG. 42 is an exploded view of a preferred embodiment of liner system 400. Liner system 400 preferably includes fracture plate 402. Preferably, fracture plate 402 includes lower surface 422. In some embodiments, recess 420 may be disposed along lower surface 422 of fracture plate 402. Recess 420 may include second set of holes 408.

Additionally, liner system 400 also preferably includes liner 404. Liner 404 may be made of a similar material to fracture plate 402. In some embodiments, liner 404 may be a wafer of bone. Using a wafer of bone may help facilitate bone to bone fusion. In some embodiments, liner 404 may include lower surface 424. Preferably, lower surface 424 includes bone growth promoting agent 426. In a preferred embodiment, lower surface 424 is disposed adjacent to bone 406. Liner 404 also preferably includes first set of holes 410.

In some embodiments, liner system 400 may also include mesh 425. Generally, mesh 425 may be treated with a bone growth promoting agent. In some embodiments, mesh 425 may be disposed between liner 404 and bone 406. In other embodiments, liner system 400 may include only mesh 425 or liner 404. In some embodiments, mesh 425 may be a bone wafer, composite, bio-compatible material or a second liner.

In some embodiments, fracture plate 402 may be constructed of a bio-absorbable material. In this manner, fracture plate 402 may eventually dissolve into the tissue surrounding it. This is a preferred situation over situations in which the fracture plate would need to be removed via surgery. In a similar manner, the fracture plate 402, the liner 404 and/or the mesh 425 may be constructed of a bio-absorbable material. Liner 404 and/or mesh 425 can be constructed of bone, collagen or other biological or bio-compatible materials. In some cases, a bone wafer may be used. Additional liners and/or meshes may be used, resulting in more than two liners and possibly more than two meshes.

Generally, recess 420 may be configured to receive liner 404. In some embodiments, recess 420 has a depth that is equivalent to the thickness of liner 404. In other embodiments, the thickness of liner 404 and the depth of recess 420 may be varied.

Preferably, liner system 400 also includes screw set 412. In some embodiments, second set of holes 408 are configured to receive screw set 412. Generally, first set of holes 410 and second set of holes 408 may be aligned.

Once assembled, liner system 400 may be configured to add support to bone 406. In particular, as liner 404 preferably includes selectively applied bone growth promoting agent 426 along lower surface 424, this may help stimulate the growth of bone 406. Generally, a liner may also include various bone growth promoting agents that may be selectively applied to various regions. The types of bone growth promoting agents and the methods of selectively applying them may be substantially similar to the previous embodiments.

In some embodiments, a fracture plate with holes may help induce bone growth that allows bone to grow into the holes. In this manner, the bone may be partially fused to the fracture plate. Preferably, the plate may include an additional bone growth promoting agent to help stimulate bone growth.

Figure 43:
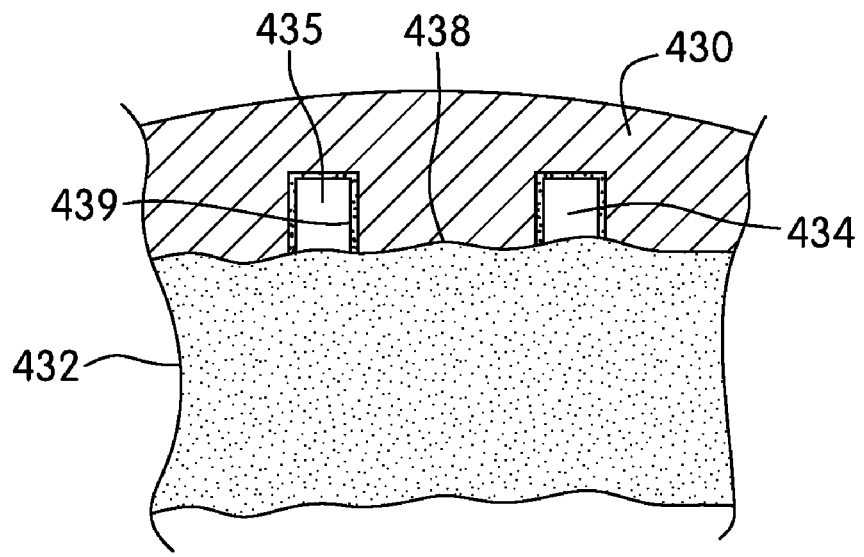
FIG. 43 is a side cross sectional view of a preferred embodiment of a fracture plate contacting a bone.
Figure 44:
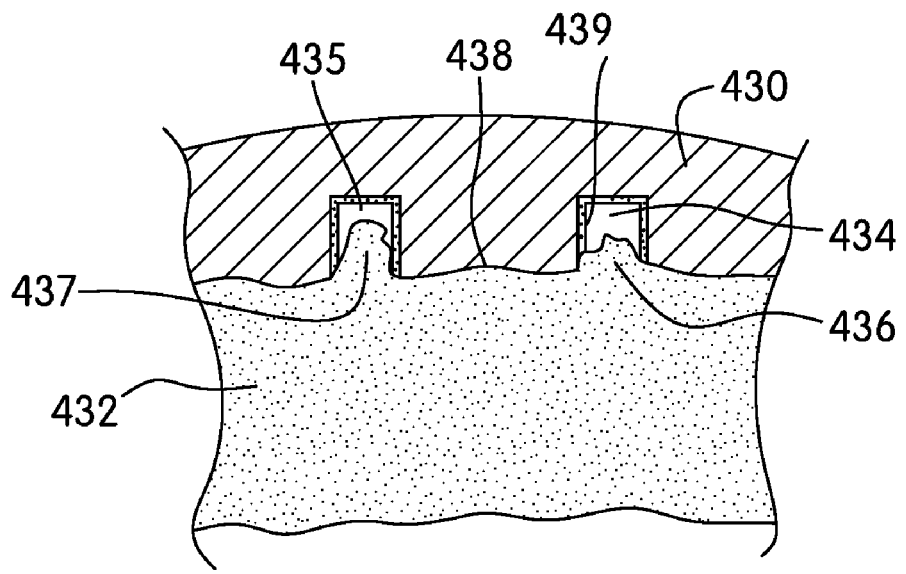
FIG. 44 is a side cross sectional view of a preferred embodiment of a fracture plate with bony fusion.

Referring to FIGS. 43-44, fracture plate 430 may preferably be configured to promote bone growth on the walls of first hole 434, second hole 435, and lower surface 438. This may be achieved with or without the use of a bone growth promoting agent. In a preferred embodiment, bone growth promoting agent 439 may be applied to holes 434 and 435. Generally, fracture plate 430 may be secured to bone 432 by some means, such as a screw. Over time, first portion 436 and second portion 437 of bone 432 may grow into first hole 434 and second hole 435. In addition, bone growth will also occur into the surfaces of first hole 434 and second hole 435. In other words, bone growth can occur on a macroscopic scale—bone growth into holes 434 and 435—and on a microscopic scale as well, bone growth onto the surfaces of holes 434 and 435 due to the bone growth promoting agent applied to the walls of holes 434 and 435.

In an alternative embodiment, the implantable prosthesis may take the form of a screw. In some cases, a screw may be configured to attach multiple bones together. In other cases, a screw may be configured to attach a rod or a fracture plate to a fractured single bone. Generally, a screw may be used with many different kinds of implantable prostheses.

In a manner similar to the rods and fracture plates discussed in the previous embodiments, a bone growth promoting agent may be selectively applied to a screw to stimulate bone growth. Because a screw has a similar structure to a rod, it follows that all of the various modifications that may be made to a rod to include selectively applied bone growth promoting agents may also be applied to the screw disclosed here. In particular, any of the bone growth agents previously disclosed may be applied to any portion of a screw. Also, these bone growth agents may be applied in the patterns disclosed in the previous embodiments.

The term screw as used here applied to any device with threading. In some cases, screws may or may not include a head. Screws can also include a solid or hollow boring tip. This solid boring tip allows the screw to be inserted into a region of bone where no previous hole has been made. Additionally, the head may be associated with a fastening tool, such as a screw driver, hex key or a drill, allowing the screw to be turned.

Figure 45:
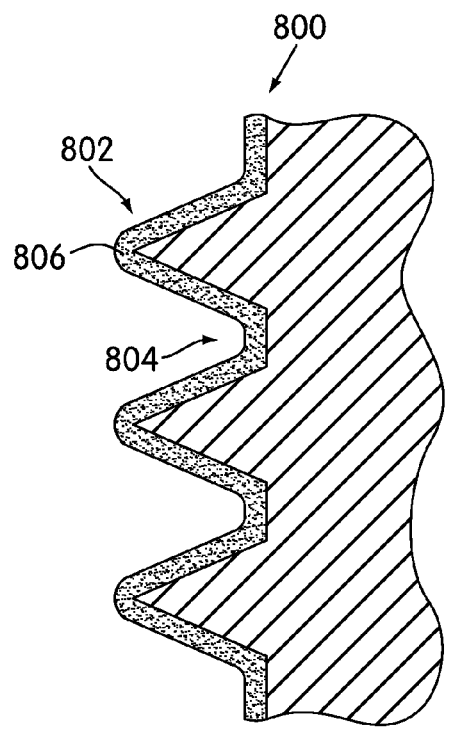
FIG. 45 is a schematic cross section of a preferred embodiment of the threading of a screw.

In FIG. 45, bone growth promoting agent 806 has been applied to threading peaks 802 of threading 800 as well as threading valleys 804 of threading 800. This coating of the entirety of threading 800 may be accomplished by dipping threading 800 in a chemical including bone growth promoting agent 806. The coating can also be applied by spraying, sintering, wax covering, as well as other suitable methods.

Figure 46:
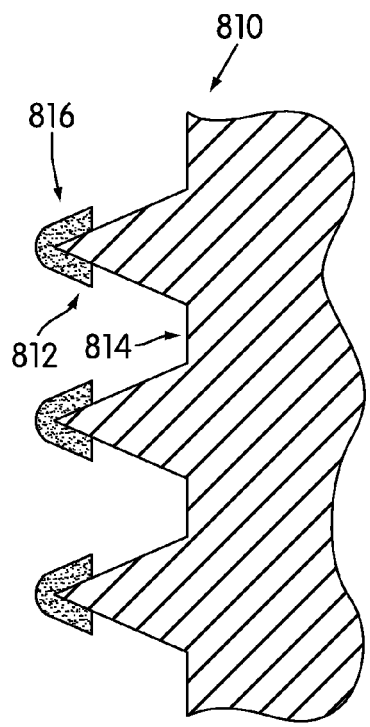
FIG. 46 is a schematic cross section of a preferred embodiment of the threading of a screw.

Additionally, it may be desirable in some cases to only coat a portion of the threading. This can provide different degrees of incorporation into the bone. In some cases, limited degrees of incorporation may be helpful to assist in later removal of the screw. Referring to FIG. 46, it may be possible to only apply bone growth promoting agent 816 to threading peaks 812 of threading 810. In this manner, threading valleys 814 may not include bone growth promoting agent 816. This feature may be accomplished by quickly dipping threading 810 into a chemical including bone growth promoting agent 816 before the chemical has time to fill into thread valleys 814. Additionally, the coating can also be applied by spraying, sintering, wax covering, as well as other suitable methods.

Figure 47:
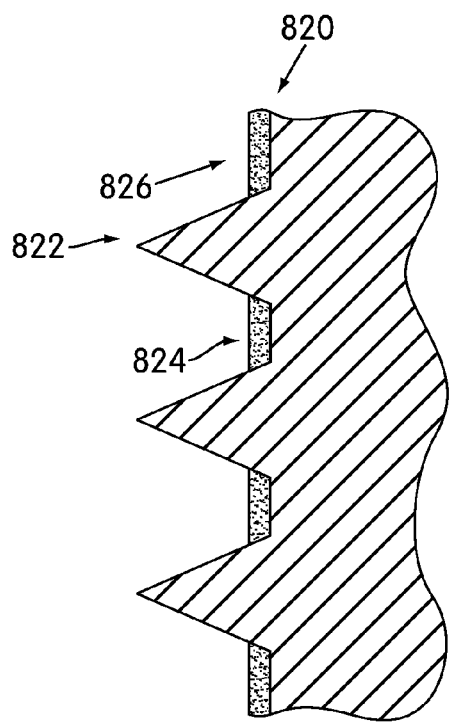
FIG. 47 is a schematic cross section of a preferred embodiment of the threading of a screw.

In some cases, only the threading valleys may be coated. Referring to FIG. 47, threading valleys 824 of threading 820 may be coated with bone growth promoting agent 826. This may be accomplished by dipping threading 820 into a chemical including bone growth promoting agent 826, and then spinning the screw in a manner that expels the bone growth promoting agent 826 from threading peaks 822. Additionally, the coating can also be applied by spraying, sintering, wax covering, as well as other suitable methods.

Figure 48:
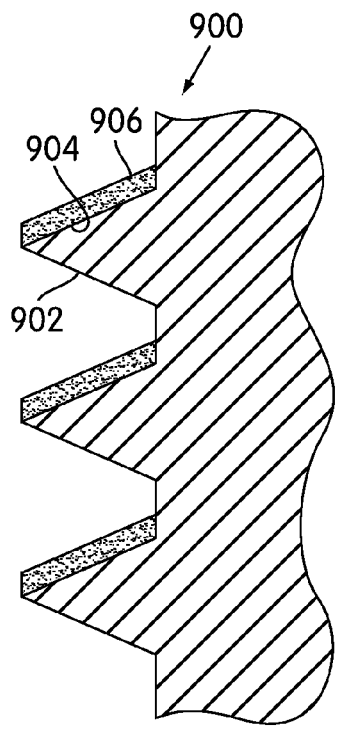
FIG. 48 is a schematic cross section of a preferred embodiment of the threading of a screw.
Figure 49:
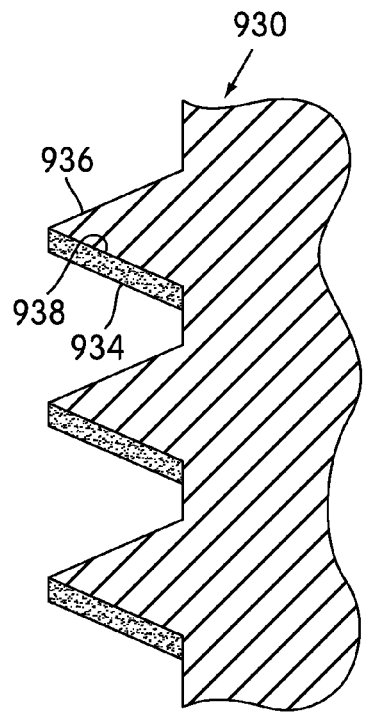
FIG. 49 is a schematic cross section of a preferred embodiment of the threading of a screw.
Figure 50:
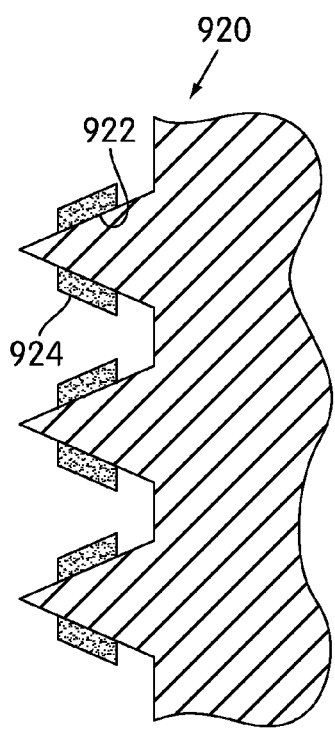
FIG. 50 is a schematic cross section of a preferred embodiment of the threading of a screw.
Figure 51:
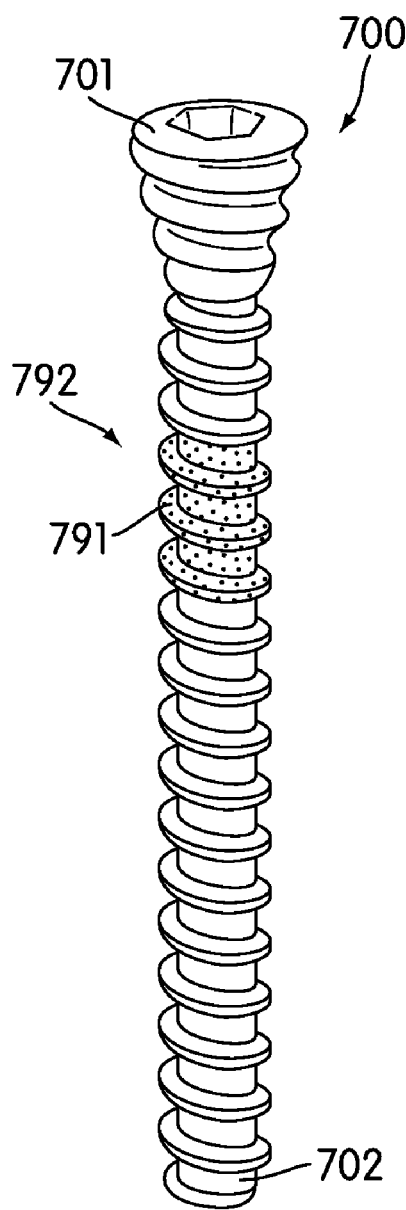
FIG. 51 is a side view of a preferred embodiment of a screw.
Figure 52:
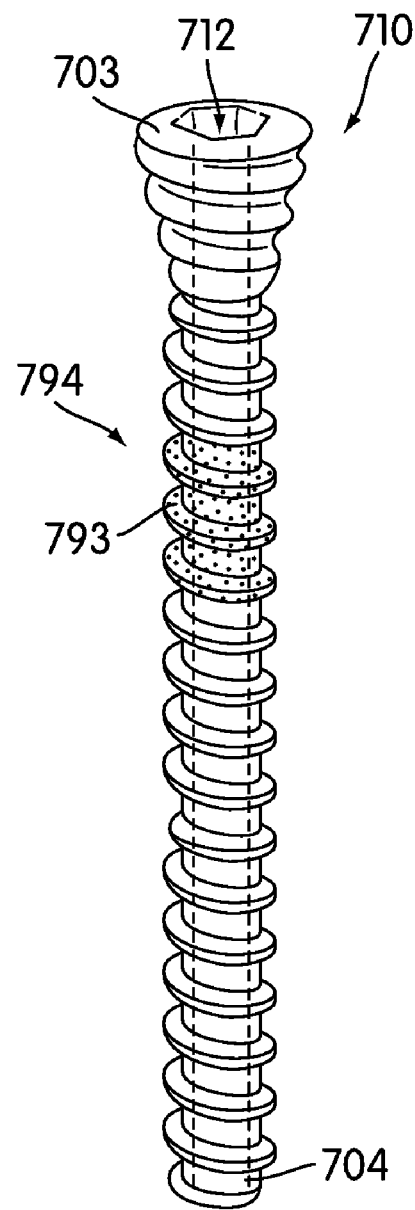
FIG. 52 is a side view of a preferred embodiment of a screw.
Figure 53:
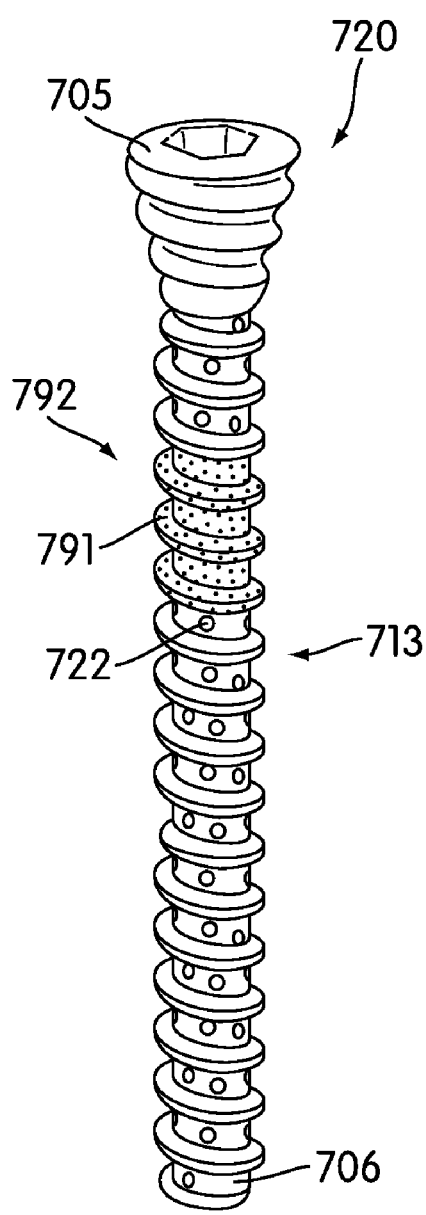
FIG. 53 is a side view of a preferred embodiment of a screw.
Figure 54:
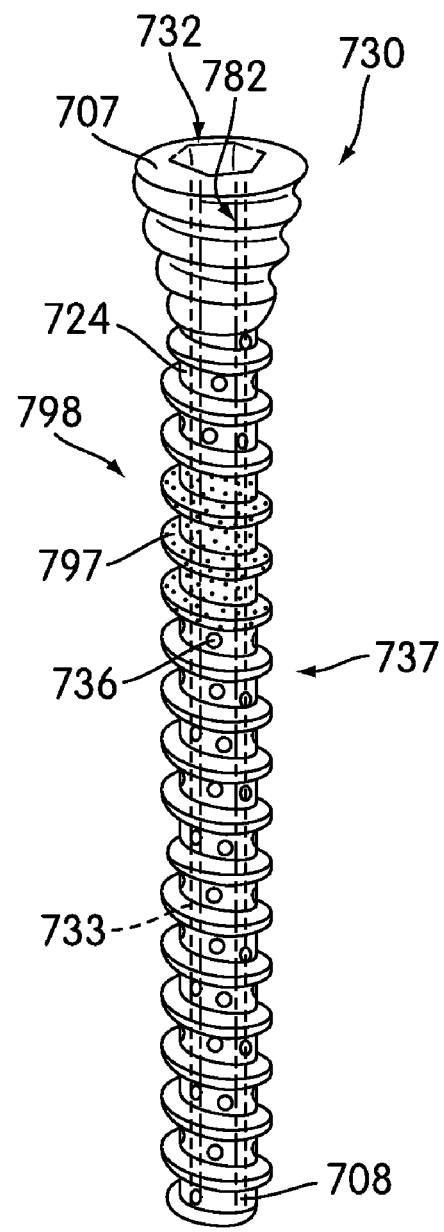
FIG. 54 is a side view of a preferred embodiment of a screw.

In other embodiments, only portions of the threading may be coated. Referring to FIG. 48, threading 900 preferably includes upper portions 904 and lower portions 902. In this embodiment, only upper portions 904 of threading 900 may be coated with bone growth promoting agent 906. Likewise, in the embodiment shown in FIG. 49, threading 930 may include upper portions 936 and lower portions 938. In this embodiment, only lower portions 938 of threading 930 may be coated with bone growth promoting agent 934. Finally, in the embodiment shown in FIG. 50, only middle portions 922 of threading 920 may be coated with bone growth promoting agent 924. As with the previous embodiments, each of the coatings may be applied using techniques such as spraying, sintering, wax covering, as well as other suitable techniques.

In some embodiments, the structure of a screw may be modified. Such modifications include hollowing out the screw, as well as adding holes to the screw. Generally, a screw may be modified in ways similar to the rods disclosed above. The screws may be fully, partially or non-cannulated screws and the coatings may be applied in whole or in part in a manner similar to the coatings applied to the rods as disclosed above.

Referring to FIGS. 51-54, screws may be configured solid, hollow, and with or without holes. One example of a hollow screw is a cannulated screw, which includes a hollow central shaft. In one embodiment, a section of screw 700 may be solid. Screw 700 also preferably includes screw head 701 and boring tip 702. In some embodiments, bone growth promoting agent 791 may be applied to first region 792. Preferably, bone growth promoting agent 791 is only applied to first region 792 and not the entire shaft of screw 700. Likewise, throughout the remaining embodiments seen in FIGS. 52-54, bone growth promoting agents have been applied only to a selected region of the screw, not to the entirety. In this manner, screw 700 may stimulate bone growth along portions of a bone disposed adjacent to first region 792.

In a second embodiment, screw 710 may include hollow central core 712. Second screw 710 may include screw head 703 and boring tip 704. In some embodiments, bone growth promoting agent 793 may be applied to first region 794. In this manner, screw 710 may stimulate bone growth along portions of a bone disposed adjacent to first region 794.

Preferably, in a third embodiment, screw 720 may include holes 722. Holes 722 are preferably disposed along a first portion 713 of screw 720. Generally, holes 722 may be any depth, any shape, angle, and have any size circumference. Similarly, the density of holes 722 may be varied in other embodiments. In some embodiments, a combination of holes having different sizes, shapes, angles or densities may be used. Preferably, screw 720 may also include screw head 705 and boring tip 706. In some embodiments, bone growth promoting agent 795 may be applied to second portion 796. In this manner, screw 720 may stimulate bone growth along portions of a bone disposed adjacent to first region 796. In a preferred embodiment, a bone growth promoting agent is not applied to screw head 705.

A fourth embodiment of a section of screw 730 may preferably include hollow central core 732 as well as holes 736. Holes 736 are preferably disposed along first portion 737 of screw 730. Generally, holes 736 may be any depth, any shape, angle, and have any size circumference. Similarly, the density of holes 736 may be varied in other embodiments. In some embodiments, a combination of holes having different sizes, shapes, angles or densities may be used. In a preferred embodiment, holes 736 may be disposed between outer surface 729 and inner surface 733 of hollow central core 732. In this manner, holes 736 preferably allow fluid communication between hollow central core 732 and outer surface 729. Preferably, fourth screw 730 may also include screw head 707 and boring tip 708. In some embodiments, bone growth promoting agent 797 may be applied to first region 798. In this manner, screw 730 may stimulate bone growth along portions of a bone disposed adjacent to first region 798. In a preferred embodiment, inner surface 733 may include bone growth promoting agent 782 as well. Bone growth promoting agent 782 applied to inner surface 733 may be similar or different than bone growth promoting agent 797 that is applied to first region 798. The various bone growth promoting agents can be selected to achieve different bone growth properties and/or to encourage different rates or kinds of bone growth. In a preferred embodiment, a bone growth promoting agent is not applied to screw head 707.

Generally, the length of the central cavities 712 and 732 of the previous embodiments may be varied. Preferably, central cavities 712 and 732 extend all the way to the bottom of screws 710 and 730. Instead, the end of screws 710 and 730 are preferably solid, as is preferable for boring into bone. Additionally, the tops of screws 710 and 730 need not be configured open. In some embodiments, the tops of screws 710 and 730 may be configured closed. Furthermore, screw heads in any embodiment may include features to mate with any desired driver. For example, the screw heads may include a slot, Phillips, star, hexagonal cavity, torx, hexagonal nut or any other desired mechanical coupling. In other embodiments, the screw does not have a head, and the shaft includes features to mate with any desired driver.

Figure 55:
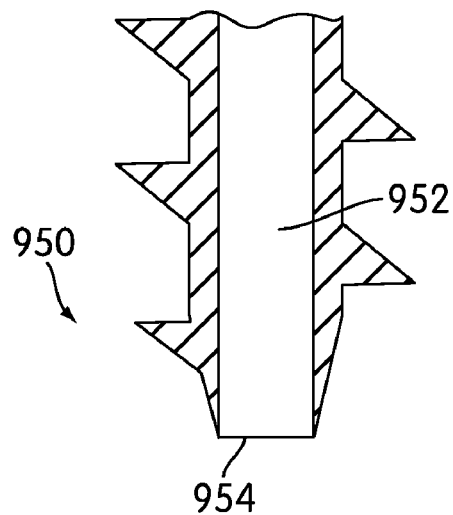
FIG. 55 is a close up cross sectional view of a screw with a hollow boring tip.
Figure 56:
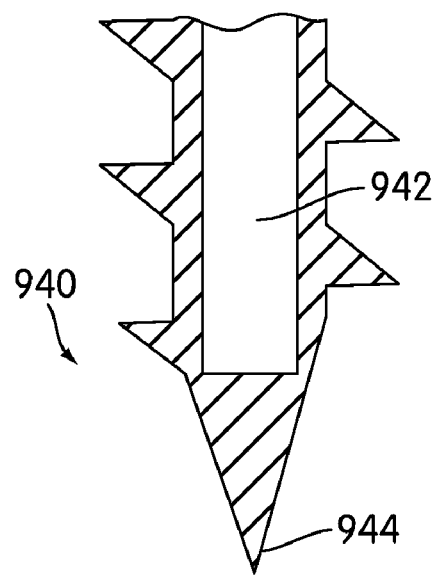
FIG. 56 is a close up cross sectional view of a screw with a solid boring tip.

Additionally, in some embodiments, the tips of the screws including bone growth promoting agents may be configured as open or closed. In other words, the tips may have a hollow or solid boring tip. Referring to FIG. 55, a screw including tip portion 950 includes central cavity 952 that extends all the way through boring tip 954. In another embodiment, seen in FIG. 56, a screw including tip portion 940 includes central cavity 942 with a solid boring tip 944.

In a manner similar to the rods and cages of the previous embodiments, a screw may be configured to promote ingrowth of bone and fuse with the bone. In some embodiments, a screw including holes and a hollow central core may be implanted into a bone. Once the screw has been implanted inside the bone, growth may occur through the holes into the hollow central core. In a preferred embodiment, the outer and inner surfaces of the screw may be coated with a bone growth promoting agent.

Figure 57:
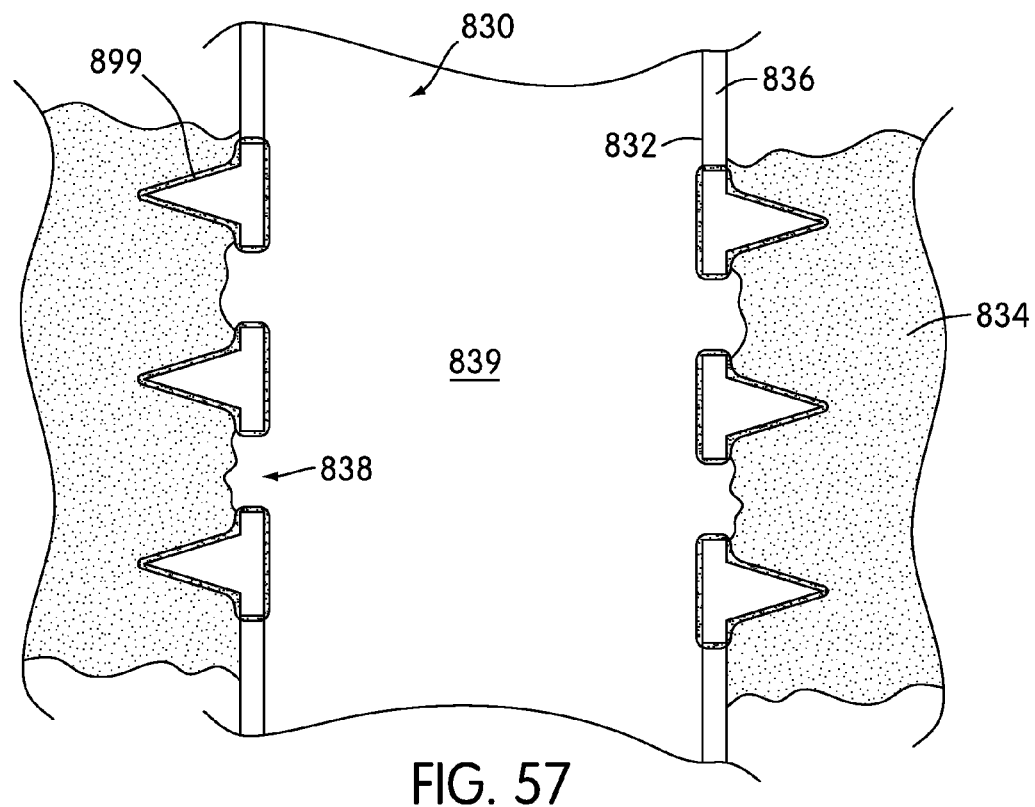
FIG. 57 is a schematic cross section of a preferred embodiment of a screw inserted into bone.
Figure 58:
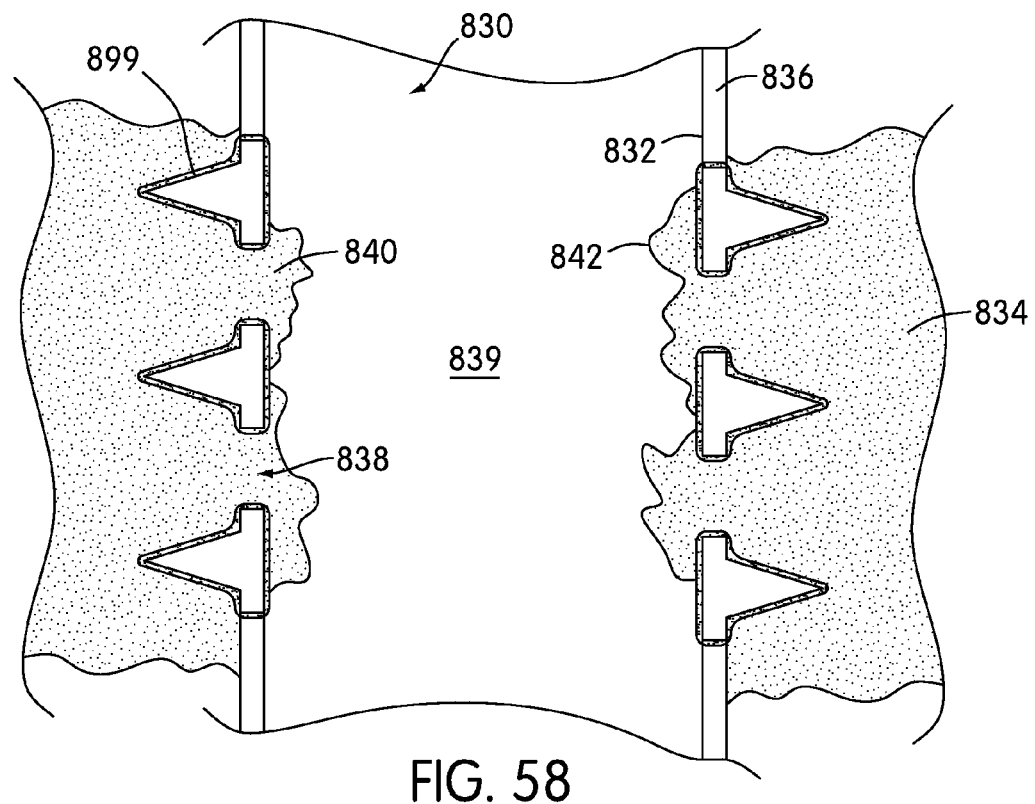
FIG. 58 is a schematic cross section of a preferred embodiment of bone growing into a hollow central core of a screw.

Referring to FIGS. 57-58, ingrowth of the bone from outer surface 836 to inner surface 832 may proceed once screw 830 has been inserted into a section of bone 834. With time, portions 840 of bone 834 may grow through holes 838 into hollow central core 839. In some embodiments, portions 840 may fuse together within hollow central core 839. In this way, screw 830 may be fused with bone 834. In a preferred embodiment, holes 838 are used in conjunction with bone growth promoting agent 899 disposed along inner surface 832 and outer surface 836 in order to induce bone growth. In some embodiments, bone growth promoting agent 899 may also be disposed within holes 838. In this manner, screw 830 may be partially or fully integrated into bone 834 as it is healing, micro and macroscopically.

Generally, rods, screws and plates may be combined in a variety of ways to create spinal fixation systems. Typically, spinal fixation systems are used to provide additional structural support to or between vertebrae. In some cases, spinal fixation systems may be associated with bone fusion between vertebrae. Spinal fixation systems may be associated with lumbar vertebrae, thoracic vertebrae as well as cervical vertebrae. In some embodiments, spinal fixation systems may be associated with combinations of lumbar, thoracic and/or cervical vertebrae. Additionally, in some embodiments, spinal fixation systems may be associated with the sacrum.

Preferably, each of these spinal fixation systems may be associated with regions of the spine where bone has been broken, fractured or damaged in some way. Therefore, it may be useful to consider the application of selectively applied bone growth promoting agents to various portions of these fixation systems. Because some portions of spinal fixation systems may extend across regions of the spine that do not require new bone growth, it is an important feature of these spinal fixation systems that the bone growth promoting agents be selectively applied. By selectively applying bone growth promoting agents, this may decrease or eliminate the possibility that new bone growth will interfere with the intended functionality of the system, as may occur in some cases where a bone growth promoting agent is applied to the entire device.

Throughout the remainder of this detailed description it should be understood that any rods disclosed are intended only as illustrative embodiments of components of various spinal fixation systems. As previously disclosed in this application, all rods may be configured as solid or hollow. Additionally, all screws may be configured as hollow or solid. Finally, the terms rods, screws and plates refer to a general category of objects. The terms rod, screw and plate are not meant to confine the current disclosure to particular embodiments that include specific geometries or various material constructions.

For clarity, the following embodiments discuss regions or portions of spinal fixation systems with selectively applied bone growth promoting agents in a generic manner. It should be understood, however, that a bone growth promoting agent may be selectively applied to each of the following systems in a manner analogous to that discussed previously for rods. In particular, a bone growth promoting agent may be applied to a rod, screw or a plate along any region, and in any pattern. Additionally, multiple different types of bone growth promoting agents may be used with rods, screws and/or plates, as well as other similar devices. Examples of these bone growth promoting agents and various coating patterns have been previously discussed.

Spinal fixation systems may include provisions for increasing bony fusion. In some embodiments, one or more components of a spinal fixation system, including rods, plates, screws and coupling devices as well as other components, may include holes. In some cases, all of the components of a spinal fixation system may include holes. In other cases, only some of the components of a spinal fixation system may include holes. In still other embodiments, none of the components of a spinal fixation system may include holes.

In some embodiments, the number, size, shape and density of the holes may vary. In some cases, a combination of macroscopic holes and microscopic holes or other bone growth promoting surface treatments can be used. By using a combination of both features, bone growth can be encouraged at the surface of the spinal fusion device so that the spinal fusion device, on a surface level, integrates with the bone; and by using macroscopic holes, large scale or bulk integration of the spinal fusion implant can occur, further solidifying the integration of the spinal fusion implant with the bone.

Furthermore, in some embodiments, the depth of each hole may vary. In some cases, some or all of the holes may penetrate deep into a surface of a rod, plate, screw or other component of a spinal fixation system. In cases where a rod or screw has a hollow core, one or more holes may penetrate through the surface of the spinal fusion device into a hollow central core of the rod, screw or other component of a spinal fixation system. In other embodiments, some or all of the holes may be shallow and only penetrate slightly into the surface of a rod, plate or screw.

In some embodiments, a selectively applied bone growth promoting agent may be applied to one or more holes associated with a rod, screw, plate or other component of a spinal fixation system. In some cases, the bone growth promoting agent may be selectively applied to only some of the holes. In some cases, the bone growth promoting agent may be applied to the bottom of a hole, the interior of the hole or some other portion of the hole.

It should be understood that any of the various configurations of holes discussed here, including combinations of these configurations, may be applied to any component of a spinal fixation system discussed in the following embodiments. Generally, any rod, plate or screw or other component of a spinal fixation system discussed in the following embodiments could include holes in some manner. In particular, bone growth promoting agents, as discussed above, may be selectively applied to one or more holes associated with a rod, plate, screw or other component of a spinal fixation system as discussed above.

FIGS. 59-62 illustrate a preferred embodiment of spinal fixation system 1299 associated with lumbar vertebrae 1290. Lumbar vertebrae 1290 preferably include multiple vertebral bodies, including first vertebral body 1297 and second vertebral body 1298. In a preferred embodiment, first vertebral body 1297 is the L4 vertebral body and second vertebral body 1298 is the L5 vertebral body. In some embodiments, spinal fixation system 1299 may also be associated with sacrum 1351.

In some embodiments, spinal fixation system 1299 may include rod 1300. Preferably, rod 1300 may be disposed along posterior side 1359 of lumbar vertebrae 1290. In this preferred embodiment, rod 1300 may extend from first vertebral body 1297 to sacrum 1351. In other embodiments, rod 1300 may extend to additional vertebrae beyond first vertebral body 1297.

Rod 1300 may have any desired geometry. In a preferred embodiment, rod 1300 may be cylindrical. In other embodiments, the cross sectional shape of rod 1300 may vary. Examples of cross sectional shapes for rod 1300 include, but are not limited to rounded, oval, hexagonal, rectangular, as well as other cross sectional shapes. Additionally, rod 1300 may be constructed to be solid, or to have a hollow core. Also, in some embodiments, rod 1300 may have macro and/or micro holes disposed along outer surface 1291 (see FIG. 60). These possible variations of rod 1300 should be understood to apply to any rod discussed throughout the rest of this detailed discussion.

Preferably, spinal fixation system 1299 also includes first screw 1292, second screw 1293, and third screw 1294. First screw body 1304 of first screw 1292 is preferably inserted into first vertebral body 1297. Likewise, second screw body 1296 of second screw 1293 is preferably inserted into second vertebral body 1298. In the preferred embodiment, third screw body 1307 of third screw 1294 may be inserted into sacrum 1351. In this embodiment, screws 1292 and 1293 may be oriented at angles close to 90 degrees, with respect to rod 1300. Third screw 1294 is preferably disposed at an obtuse angle with respect to rod 1300.

It should be understood that screws 1292-1294 could be any type of screw configured to insert into a vertebral body. Screws 1292-1294 may be configured as solid, hollow or cannulated. In other embodiments, screws 1292-1294 could include macro holes to increase macro fixation of bone as well as micro holes to increase micro fixation of bone. These configurations may help to increase surface area for fusion as well as help to increase healing rates associated with spinal fixation system 1299.

Although the preferred embodiment includes three screws associated with spinal fixation system 1299, in other embodiments, more or less than three screws may be used in conjunction with rod 1300. In some embodiments, for example, only two screws may be used. For example, in another embodiment, spinal fixation system 1299 may include only first screw 1292 (associated with first vertebral body 1297) and second screw 1293 (associated with second vertebral body 1298). In other embodiments, more than three screws may be used. Furthermore, the configuration described here could be extended in scoliosis to include multiple levels of screws, as well as plates and/or hooks.

Additionally, in some embodiments, spinal fixation system 1299 may comprise a plate associated with multiple screws, rather than a rod with multiple screws. Generally, any number of plates could be used in conjunction with screws to form a spinal fixation system associated with lumbar vertebrae 1290.

Generally, first screw 1292, second screw 1293 and third screw 1294 may be attached to rod 1300 via first coupling device 1305, second coupling device 1295 and third coupling device 1306. First coupling device 1305, second coupling device 1295 and third coupling device 1306 may be any devices that fix first screw 1292, second screw 1293 and third screw 1294 in place with respect to rod 1300.

Generally, any type of screw to rod coupling system may be used. In some embodiments, a fixed coupling system may be used to keep the screws fixed in place with respect to the rod. In other embodiments, a coupling device configured for a polyaxial screw may be used that allows the screw some range of motion along different axes relative to the coupling device.

Preferably, spinal fixation system 1299 may include provisions for promoting bone growth and/or bony fusion. In some embodiments, spinal fixation system 1299 may be associated with a bone growth promoting agent. In a preferred embodiment, each of the components comprising spinal fixation system 1299 may include one or more bone growth promoting agents.

Figure 60:
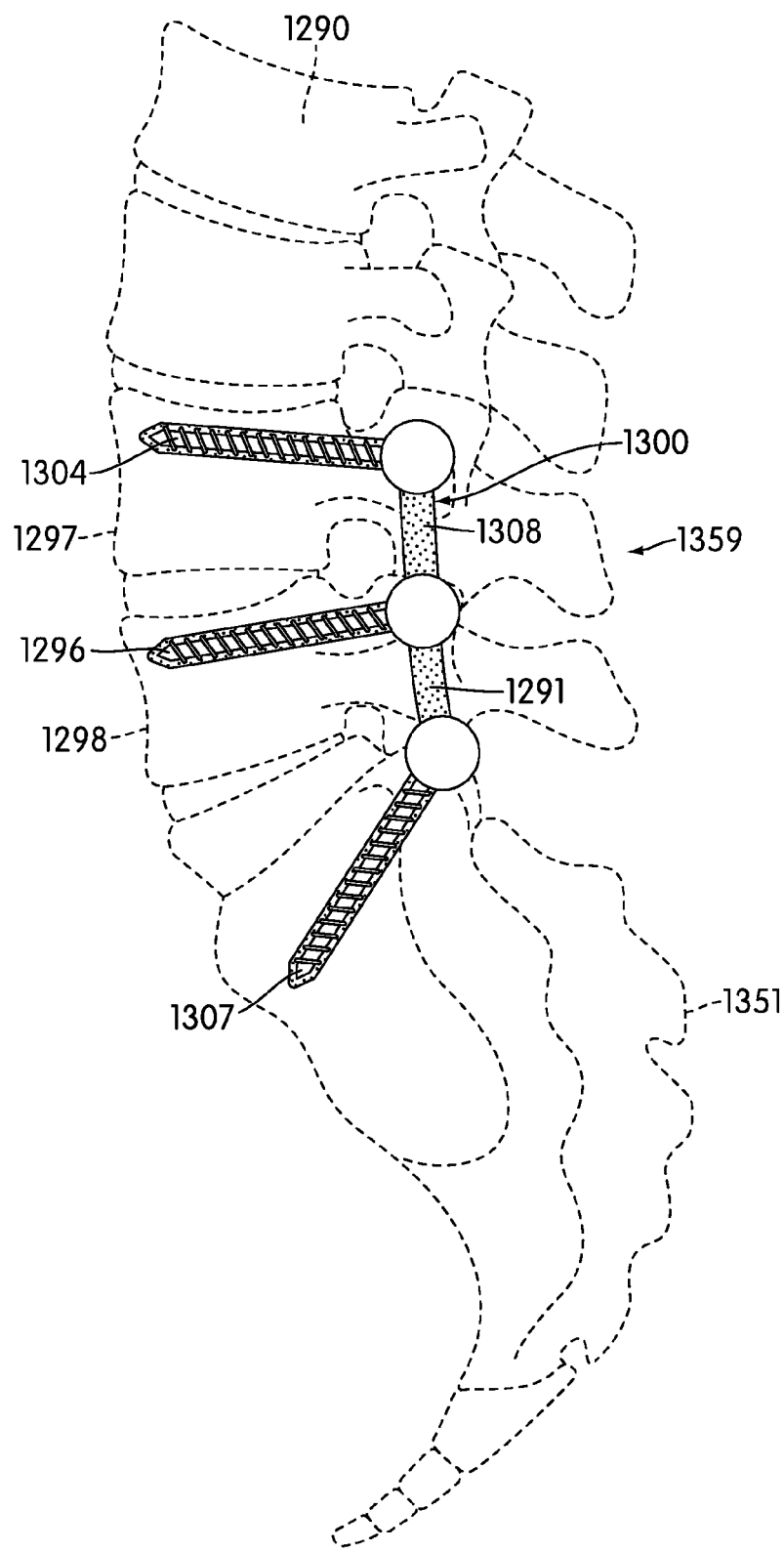
FIG. 60 is a side view of a preferred embodiment of a spinal fixation system with selectively applied bone growth promoting agents.
Figure 61:
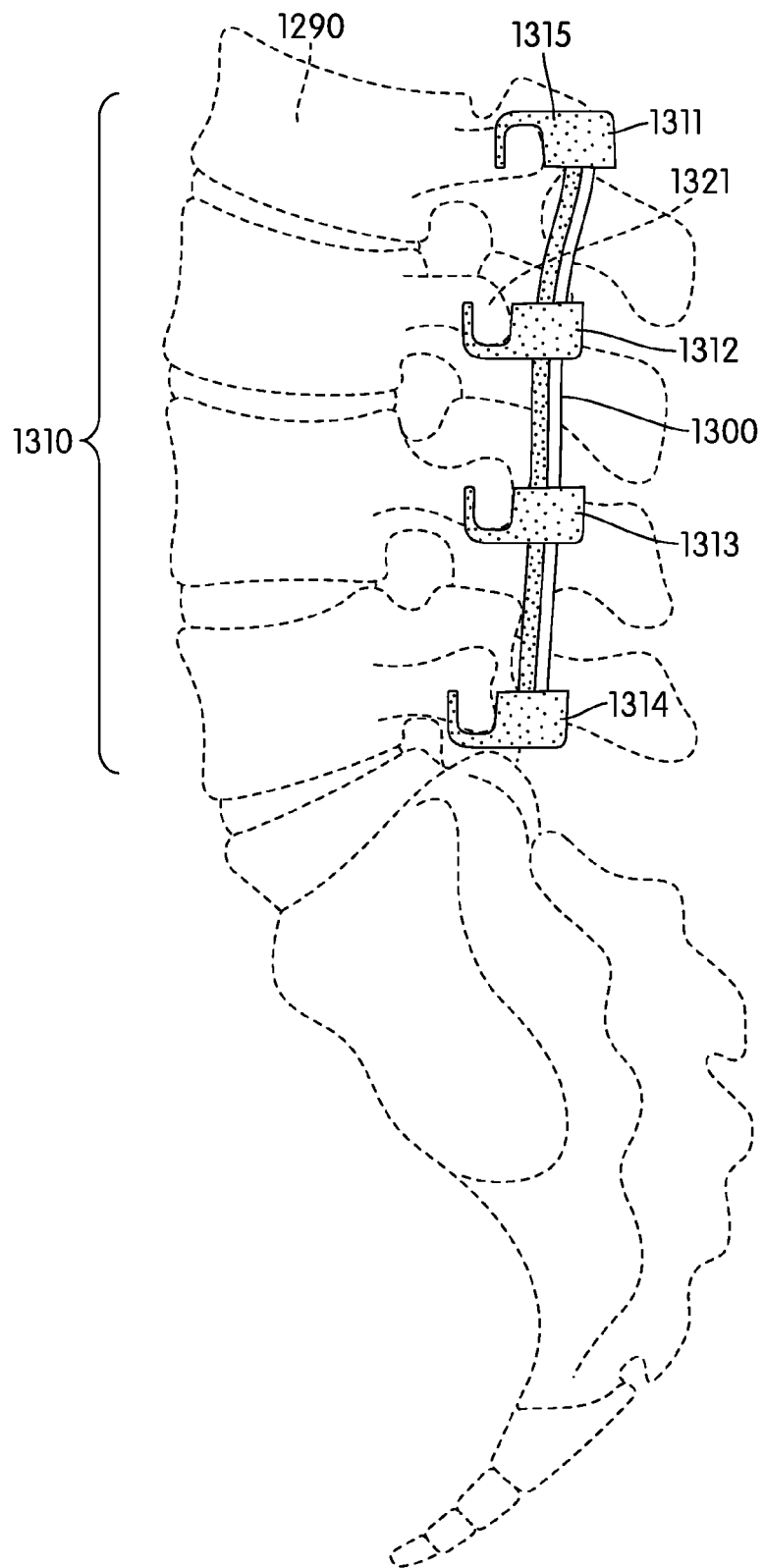
FIG. 61 is a side view of a preferred embodiment of a spinal fixation system with selectively applied bone growth promoting agents.

Preferably, rod 1300 includes first region 1301 and second region 1302. In this embodiment, first region 1301 is disposed closer to lumbar vertebrae 1290 than second region 1302. In a preferred embodiment, first region 1301 may include selectively applied first bone growth promoting agent 1308. First region 1301 may be fully or partially coated with first bone growth promoting agent 1308. In some embodiments, multiple bone growth promoting agents may be applied to first region 1301. It should be understood that first region 1301 is only intended as an example, and in other embodiment any region of rod 1300 could be coated with a bone growth promoting agent. In some embodiments, for example, the entirety of rod 1300 could include first bone growth promoting agent 1308, as shown in FIG. 60.

Figure 59:
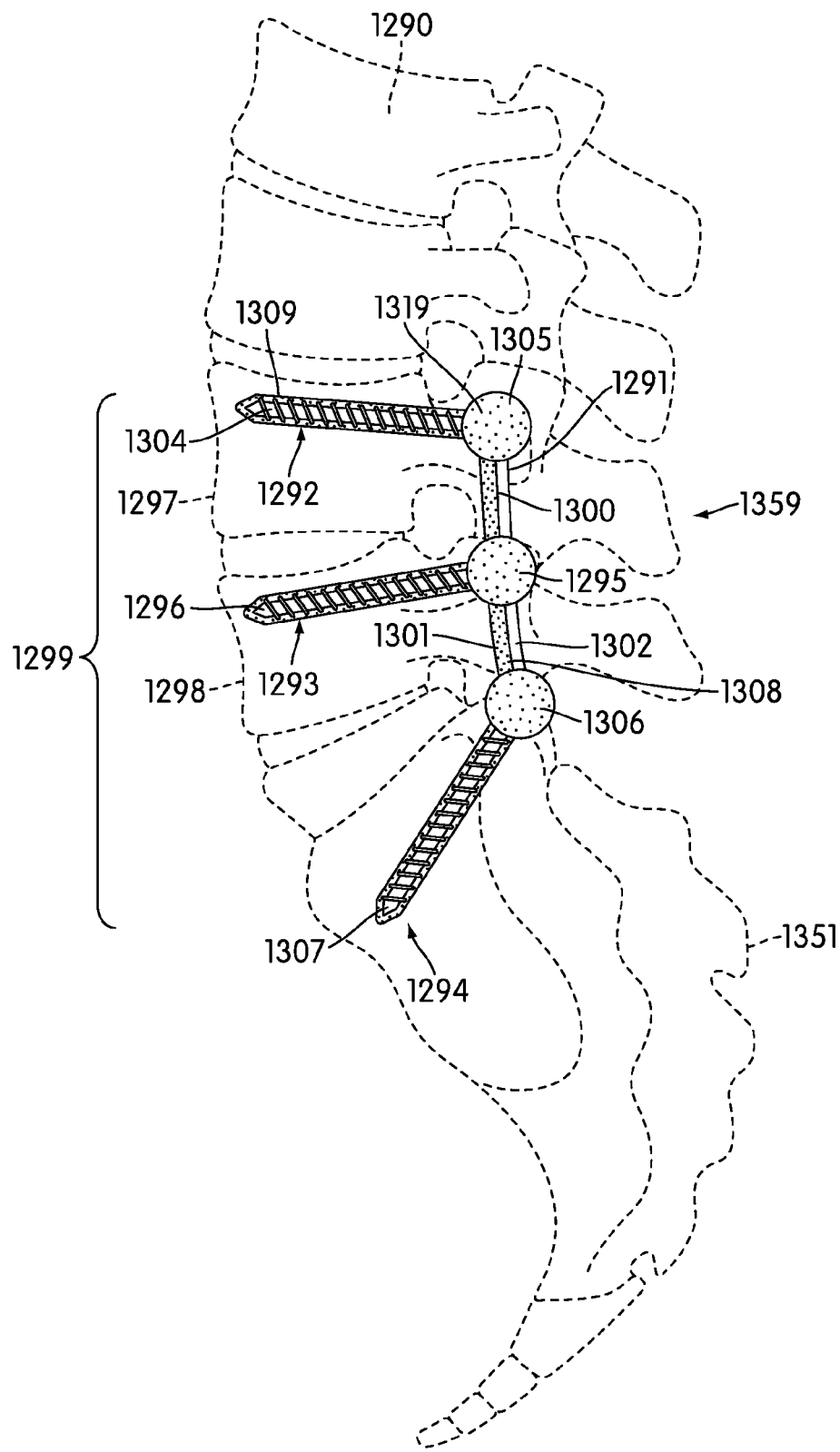
FIG. 59 is a side view of a preferred embodiment of a spinal fixation system with selectively applied bone growth promoting agents.

In the preferred embodiment, shown in FIG. 59, screws 1292-1294 may also include a selectively applied bone growth promoting agent. In particular, screw bodies 1304, 1296 and 1307 may include a selectively applied second bone growth promoting agent 1309. In some embodiments, second bone growth promoting agent 1309 may be applied to a single screw, or any combination of screws 1292-1294. Additionally, in other embodiments, second bone growth promoting agent 1309 could be applied to only the threading of screws 1292-1294 or only the surfaces of screws 1292-1294 between the threading of screws 1292-1294, as previously discussed.

Preferably, coupling devices 1305, 1295 and 1306 may also include selectively applied third bone growth promoting agent 1319. In some embodiments, third bone growth promoting agent 1319 may be applied to a single coupling device. In other embodiments, third bone growth promoting agent 1319 may be applied to any combination of coupling devices 1305, 1295 and 1306. In this preferred embodiment, third bone growth promoting agent 1319 may be applied to all three coupling devices 1305, 1295 and 1306.

Using this configuration, spinal fixation system 1299 preferably provides rigid support to the damaged region of lumbar vertebrae 1290 after surgical correction is performed. Additionally, first bone growth promoting agent 1308 and second bone growth promoting agent 1309 preferably help to stimulate bone growth along first region 1301 of rod 1300 and screw bodies 1304, 1296, and 1307, which are all disposed close to, or in contact with, lumbar vertebrae 1290. This preferably allows bone to heal to fixation devices, or to form in these regions.

In some embodiments, the anatomy of the spine may not allow for the use of screws. In some cases, hooks may be used instead of screws. In the embodiment shown in FIG. 61, spinal fixation system 1310 preferably includes first hook 1311, second hook 1312, third hook 1313, and fourth hook 1314. First hook 1311, second hook 1312, third hook 1313 and fourth hook 1314 preferably attach to lumbar vertebrae 1290 at lamina 1321. In this embodiment, hooks 1311-1314 may be attached to rod 1300 by coupling mechanisms similar to those disclosed in the previous embodiments. Generally, the types of coupling mechanisms used may vary. Additionally, as with the previous embodiment, the number of hooks used with spinal fixation system 1310 may vary.

Preferably, hooks 1311-1314 include provisions for fusing directly to lamina 1321 of lumbar vertebrae 1290. In some embodiments, bone growth promoting agent 1315 may be selectively applied to portions of hooks 1311-1314. With this preferred configuration, bone growth promoting agent 1315 preferably facilitates bone growth along the spine. This new bone growth may eventually lead to fusion between spinal fixation system 1310 and lumbar vertebrae 1290.

Figure 62:
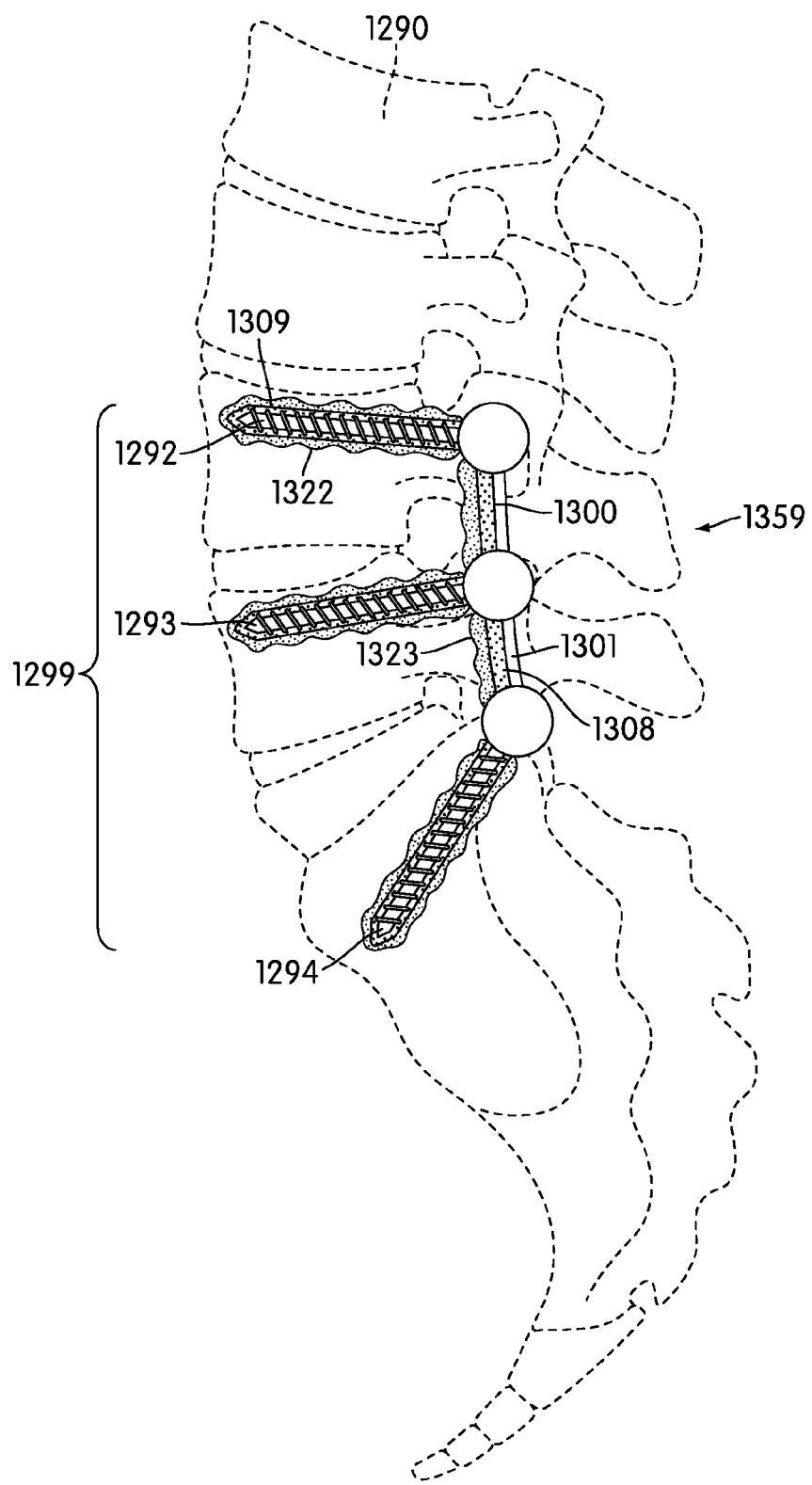
FIG. 62 is a side view of a preferred embodiment of a spinal fixation system with bone growth.

Referring to FIG. 62, new bone growth of a preferred embodiment of spinal fixation system 1299 may be observed. The current embodiment refers to bone growth for a spinal fixation system including rods and screws, however a similar type of bone growth may occur with a spinal fixation system incorporating plates and/or hooks. In this embodiment, first new bone growth 1322 may be observed along first screw 1292, second screw 1293 and third screw 1294 where second bone growth promoting agent 1309 has been previously applied. Additionally, second new bone growth 1323 may be observed along first region 1301 of rod 1300 where first bone growth promoting agent 1308 has been previously applied. With this arrangement, spinal fixation system 1299 may be partially fused to, and/or incorporated with, lumbar vertebrae 1290. This arrangement is preferred to prior designs where spinal fixation systems do not facilitate new bone growth, or are not configured to promote bony fusion only at particular portions of the spinal fixation system.

This preferred arrangement preferably creates a rebar effect, reinforcing the strength of the connection between adjacent vertebrae. This arrangement also helps to incorporate the various components of spinal fixation system 1299 into the bone or bones. This design is advantageous over previous technologies that only allow for fixation of adjacent vertebrae using a fixation system, but not the incorporation of one or more components of the fixation system into the bone to augment fusion or healing.

Generally, spinal fixation systems using screws or hooks may be associated with a particular side of the spine. In the previous embodiments, for purposes of clarity, the spinal fixation systems were associated with the left half of posterior side 1359 of lumbar vertebrae 1290. In other embodiments, the spinal fixation systems may be associated with the right side of the spine. In some cases, a surgeon may decide to use a pair of spinal fixation systems. Therefore, in some embodiments, a second spinal fixation system, substantially similar to the first in all respects, may be associated with the right half of posterior side 1359 of lumbar vertebrae 1290. Throughout the remainder of this disclosure, all fixation systems are shown as a single fixation system disposed on a particular side of the spine. It should be kept in mind, however, that each of these fixation systems could also be placed along the opposite side of the spine and in many cases a pair of fixation systems could be used along both the right and left sides of the spine, especially on the posterior side of the spine.

Also, while the previous embodiments included spinal fixation systems associated with the posterior side of lumbar vertebrae 1290, in other embodiments, spinal fixation systems may be associated with other sides of lumbar vertebrae 1290. In some embodiments, a spinal fixation system similar to the embodiments shown here, including a selectively applied bone growth promoting agent, may be associated with a lateral side of lumbar vertebrae 1290. In other embodiments, a spinal fixation system similar to the embodiments shown here, including a selectively applied bone growth promoting agent, may be associated with an anterior side of lumbar vertebrae 1290. Finally, spinal fixation system 1299, including the variations discussed in this detailed description, could also be configured to attach to both thoracic and cervical vertebrae in some embodiments.

In another embodiment, a spinal fixation system may be applied to the cervical area of the spine. The spinal fixation system may include a rod as well as screws. In a preferred embodiment, one or more bone growth promoting agents may be applied to a portion of the spinal fixation system.

The following preferred embodiment of a spinal fixation system uses a rod and screws. However, it should be understood that in other embodiments, a plate could also be used. In some cases, a plate could be used instead of a rod. In other cases, plates and rods may both be used with screws in a spinal fixation system.

Figure 63:
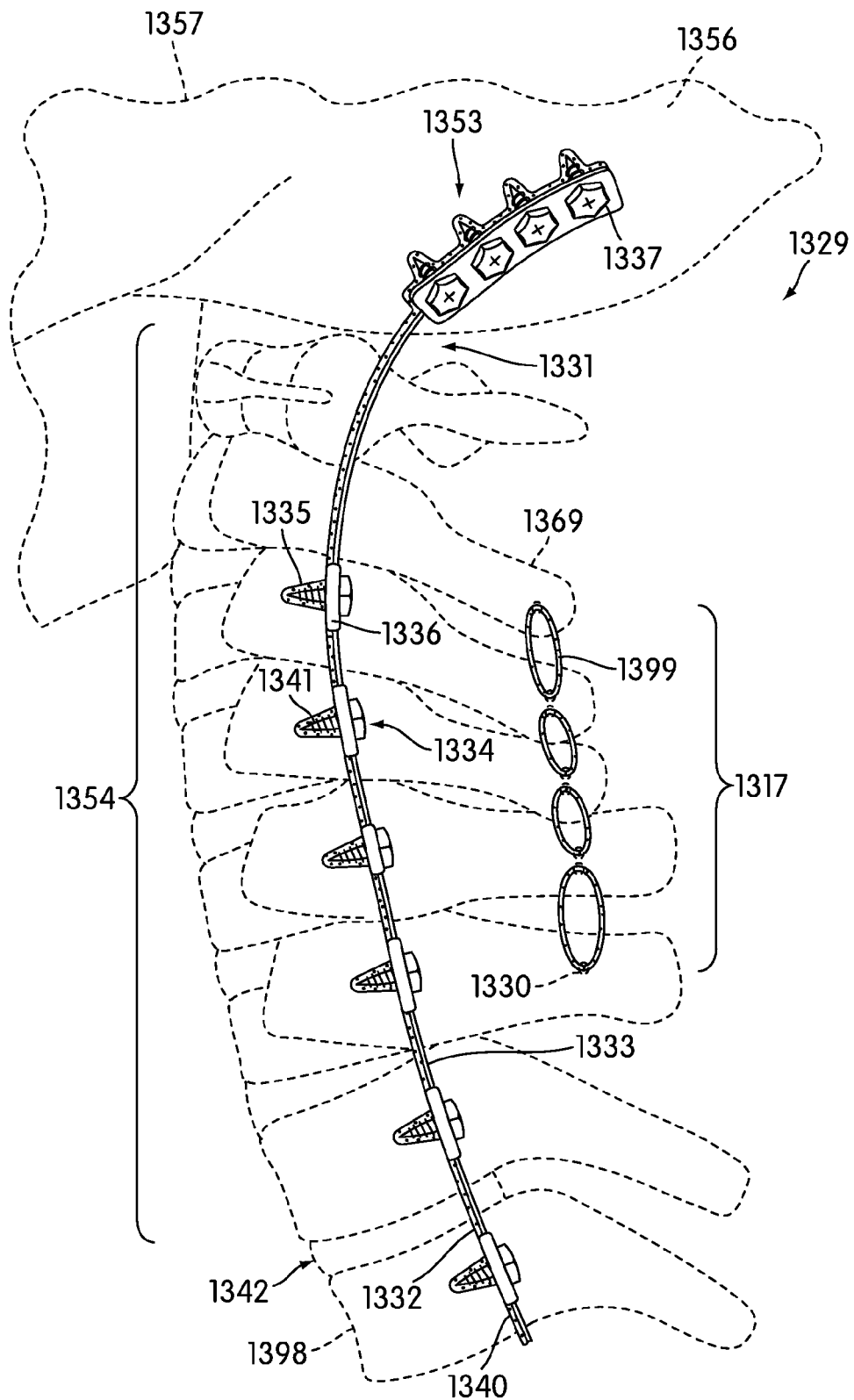
FIG. 63 is a side view of a preferred embodiment of a spinal fixation system with selectively applied bone growth promoting agents.
Figure 64:
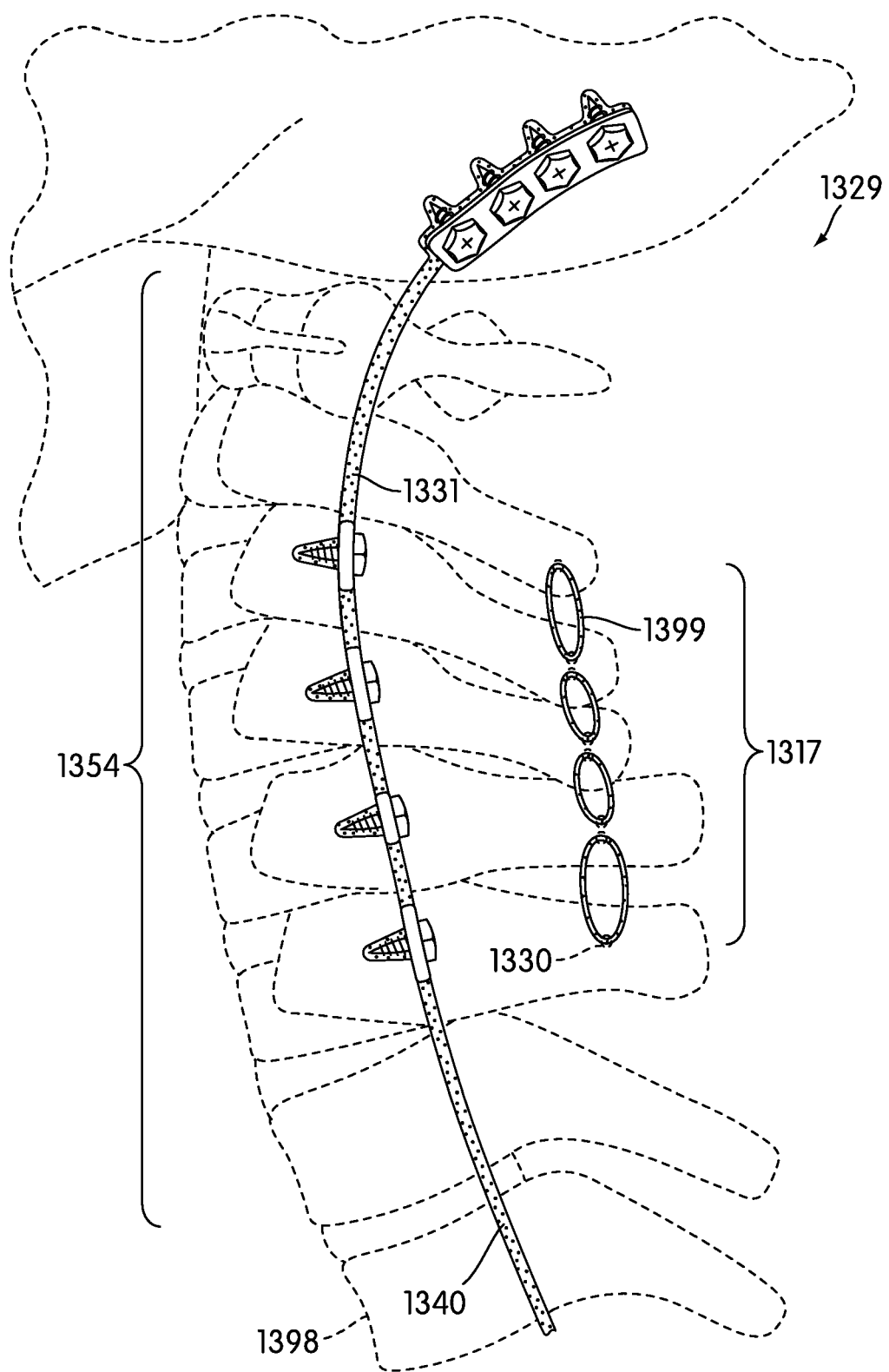
FIG. 64 is a side view of a preferred embodiment of a spinal fixation system with selectively applied bone growth promoting agents.
Figure 65:
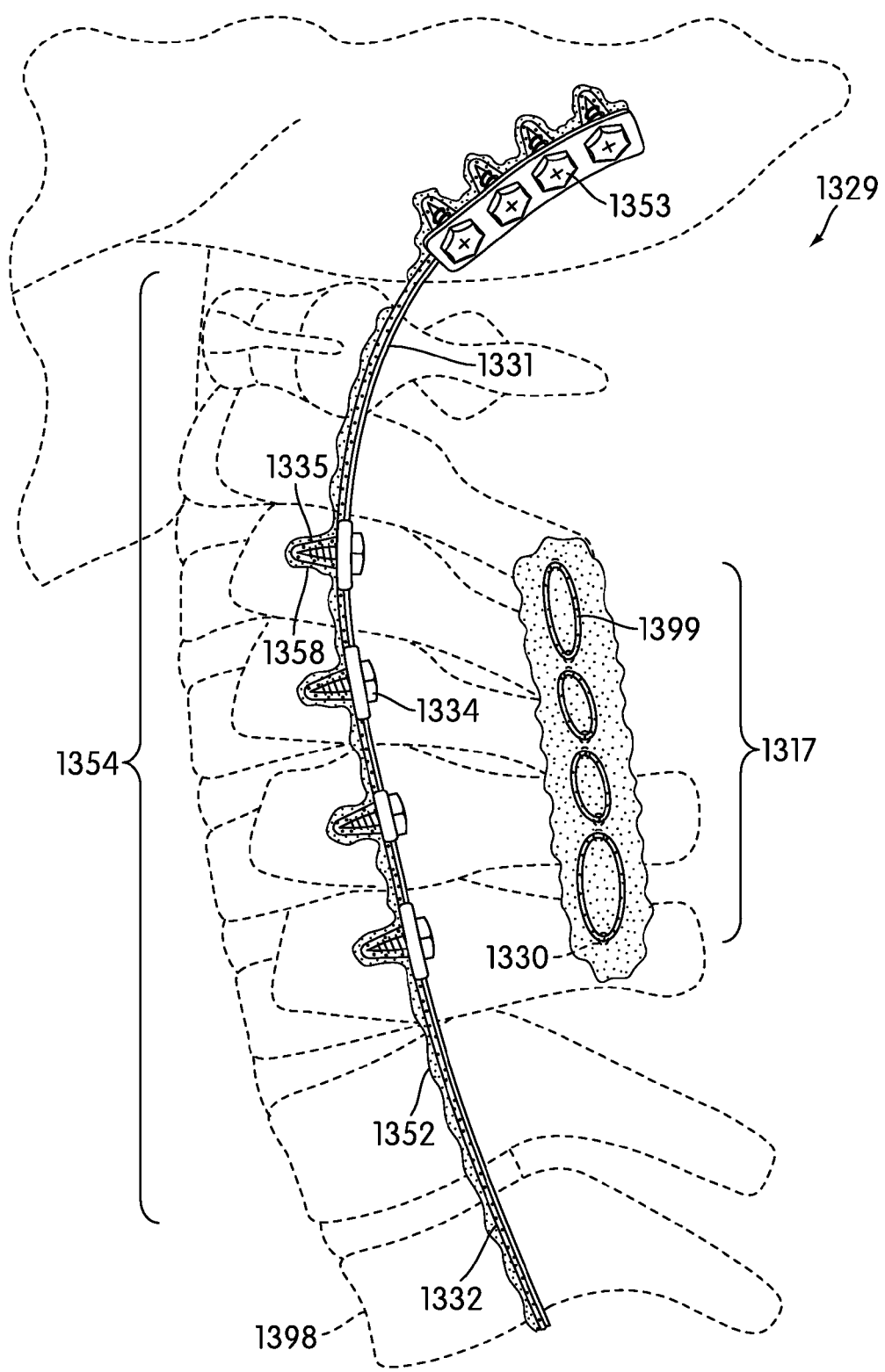
FIG. 65 is a side view of a preferred embodiment of a spinal fixation system with bone growth.

FIGS. 63-65 are a preferred embodiment of spinal fixation system 1329. In the current embodiment, spinal fixation system 1329 is a cervical fixation system. Spinal fixation system 1329 may be associated with first portion 1356 of skull 1357. In some embodiments, first portion 1356 is the occipital bone. Spinal fixation system 1329 is also preferably associated with cervical vertebrae 1354.

In this embodiment, spinal fixation system 1329 preferably includes rod 1331. Generally, rod 1331 may extend from first portion 1356 of skull 1357 to lower portion 1342 of cervical vertebrae 1354. In some cases, rod 1331 may extend below lower portion 1342 of cervical vertebrae 1354. In other embodiments, rod 1331 may only extend to an intermediate portion of cervical vertebrae 1354. However, in other embodiments, rod 1331 may extend to thoracic vertebra 1398 and, in some cases, additional thoracic vertebrae as well.

Preferably, rod 1331 may be associated with various screws that fix rod 1331 into place along cervical vertebrae 1354. In this embodiment, rod 1331 may be associated with first screw set 1334 and second screw set 1353. Each screw of first screw set 1334 and second screw set 1353 may be fixed to rod 1331 through first coupling mechanism set 1336 and second coupling mechanism set 1337, respectively. Examples of such coupling mechanisms have been described in prior embodiments. For the purposes of the current embodiment, any type of coupling device could be used.

First screw set 1334 may be associated with cervical vertebrae 1354. In some embodiments, the screws comprising first screw set 1334 may be inserted into the lateral mass of cervical vertebrae 1354 or the pedicles of cervical vertebrae 1354. Second screw set 1353 may be inserted into first portion 1356 of skull 1357. Generally, the number of screws in each screw set, 1334 and 1353, may vary. In this embodiment, both first screw set 1334 includes six screws and second screw set 1353 includes four screws.

Preferably, spinal fixation system 1329 includes provisions for facilitating new bone growth. In some embodiments, rod 1331 may include first portion 1332 and second portion 1333. Preferably, first portion 1332 is disposed closer to cervical vertebrae 1354 than second portion 1333. In this embodiment, first portion 1332 includes selectively applied first bone growth promoting agent 1340. In other embodiments, first bone growth promoting agent 1340 may be applied to the entirety of rod 1331, as seen in FIG. 64. In an alternative embodiment including a plate instead of a rod, a bone growth promoting agent may be selectively applied to the plate as well.

Referring to FIG. 63, in some embodiments, first screw set 1334 and second screw set 1353 may also include a bone growth promoting agent. Preferably, screws comprising first screw set 1334 and second screw set 1353 include screw bodies 1335. Screw bodies 1335 are preferably threaded, and anchor rod 1331 into place as it is inserted into cervical vertebrae 1354. In a preferred embodiment, second bone growth promoting agent 1341 may be selectively applied along screw bodies 1335. In other embodiments, only portions of screw bodies 1335 (including either the threading or the intermediate surfaces between the threading) may be associated with second bone growth promoting agent 1341.

In some embodiments, the use of cables associated with spinal fixation system 1329, or independently of spinal fixation system 1329, may help increase the rate of healing. Referring to FIGS. 63-65, in some embodiments cables 1317 may be associated with spinous processes 1369 or lamina of cervical vertebrae 1354. Cables 1317 may be inserted through small holes 1330 of adjacent spinous processes comprising spinous processes 1369 that have been drilled into spinous processes 1369 or made using another method. In other embodiments, cables 1317 may be looped around lamina or spinous processes of cervical, thoracic or lumbar bodies to provide fixation and augment fusion. Cables 1317 are preferably tied in loops to hold adjacent vertebrae of cervical vertebrae 1354 together during healing. In a preferred embodiment, cables 1317 may include bone growth promoting agent 1399, which may facilitate the fusing of cables 1317 to spinous processes 1369. This preferred arrangement may facilitate increased healing rates by allowing additional bone growth between adjacent vertebrae.

Spinal fixation system 1329 preferably provides rigid support to the spine after surgical correction is performed. Using one or more bone growth promoting agents along spinal fixation system 1329 preferably facilitates new bone growth. Specifically, in this embodiment, new bone growth is preferably accomplished along screw bodies 1335 and first portion 1332 of rod 1331. Referring to FIG. 65, first new bone growth 1352 can be observed along first portion 1332 of rod 1331. Likewise, second new bone growth 1358 can be observed along screw bodies 1335 of first screw set 1334 and second screw set 1353 and on cables 1317. With this configuration, spinal fixation system 1329 may be fused with cervical vertebrae 1354, thoracic vertebrae 1398 and skull 1356 (see FIG. 63), allowing for continuous structural support.

This preferred arrangement preferably creates a rebar effect, reinforcing the strength of the connection between adjacent vertebrae. This arrangement also helps to incorporate the various components of spinal fixation system 1329 into the bone or bones. This design is advantageous over previous technologies that only allow for fixation of adjacent vertebrae using a fixation system, but not the incorporation of one or more components of the fixation system into the bone to augment fusion or healing.

As with the rods in the previous embodiments, bone growth promoting agents may be applied to plates used with spinal fixation systems. These bone growth promoting agents may be applied to the entire surface of the plate or may be selectively applied to various regions of the plate surface. With this arrangement, different portions of a bone in contact with a plate may be stimulated to grow differently.

Generally, a bone growth promoting agent may be applied to any portion of a plate. Additionally, a bone growth promoting agent may be disposed in any pattern along a plate. Examples of bone growth promoting agents and patterns that may be associated with plates have been previously discussed. The use of plates with selectively applied bone growth promoting agents may be useful, for example, to promote new bone fusion across an interbody space or where only some parts of a vertebral body are damaged and require new bone stimulation.

Figure 66:
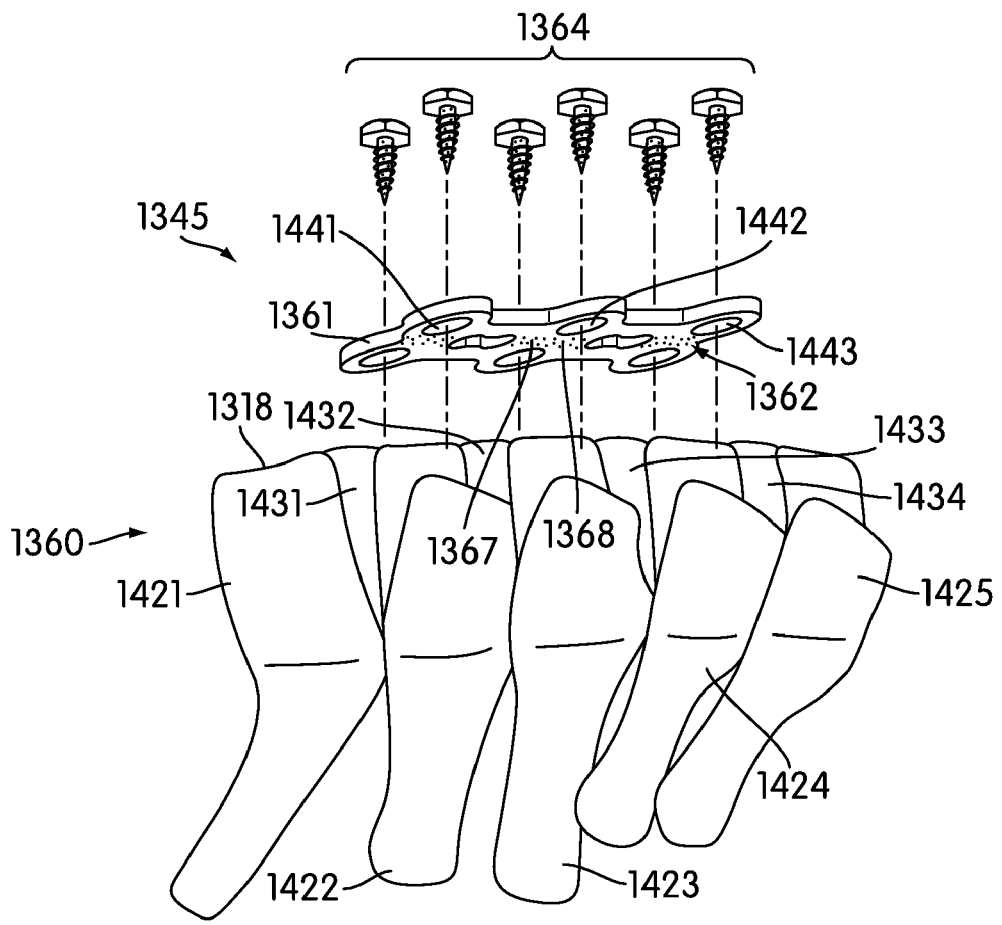
FIG. 66 is a schematic view of a preferred embodiment of a plate with selectively applied bone growth promoting agents.
Figure 67:
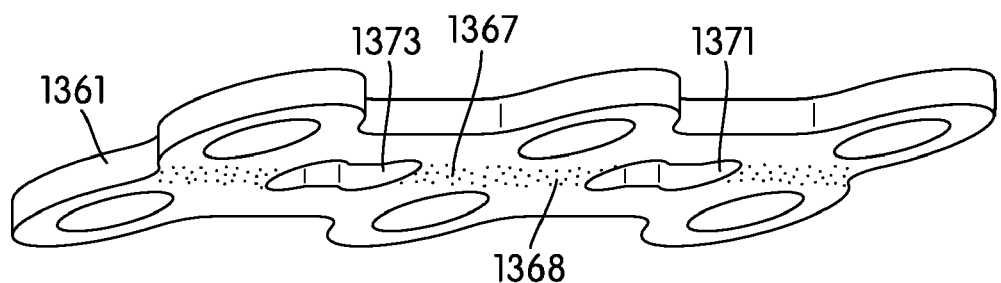
FIG. 67 is an isometric view of a preferred embodiment of a plate with selective regions including bone growth promoting agents.

Referring to FIGS. 66-67, spinal fixation system 1345 may be associated with anterior side 1318 of vertebrae 1360. Vertebrae 1360 may be any type of vertebrae, including lumbar vertebrae, thoracic vertebrae and/or cervical vertebrae. In some embodiments, vertebrae 1360 may include vertebrae of more than one type. In this preferred embodiment, vertebrae 1360 preferably comprise first vertebral body 1421, second vertebral body 1422, third vertebral body 1423, fourth vertebral body 1424 and fifth vertebral body 1425. Additionally, vertebrae 1360 may be associated with first interbody space 1431, second interbody space 1432, third interbody space 1433 and fourth interbody space 1434. These interbody spaces 1431-1434 are generally associated with discs.

In some embodiments, spinal fixation system 1345 may comprise plate 1361. Plate 1361 may have any shape, including any length, width or thickness. In this preferred embodiment, plate 1361 has a length configured so that it spans three vertebrae 1422-1424 and interbody spaces 1432 and 1433.

Preferably, plate 1361 includes first hole set 1441, second hole set 1442 and third hole set 1443, associated with second vertebral body 1422, third vertebral body 1423 and fourth vertebral body 1424, respectively. Generally, sets of holes 1441-1443 may be configured to receive screws 1364. Screws 1364 may be inserted into vertebral bodes 1422-1424. This preferred arrangement allows plate 1361 to fix vertebral bodes 1422-1424 in place with respect to one another.

In some embodiments, the number of holes comprising sets of holes 1441-1443 and the number of screws comprising screws 1364 may vary. In this preferred embodiment, there are six holes and six screws. In another embodiment, for example, there may only be four holes and four screws. This alternate configuration may be used when only two vertebrae are being fused, rather than three vertebrae as with the current embodiment.

In this embodiment, plate 1361 includes first surface 1362. Generally, first surface 1362 may be disposed adjacent to vertebrae 1360. In a preferred embodiment, first surface 1362 may be configured to contact vertebrae 1360. In some embodiments, first surface 1362 may include region 1368. Preferably, region 1368 includes bone growth promoting agent 1367.

As screws 1364 are inserted through sets of holes 1441-1443 and into vertebral bodies 1422-1424, plate 1361 may be fixed against vertebrae 1360. Using this configuration, bone growth promoting agent 1367, disposed along region 1368 preferably facilitates bone growth along vertebrae 1360. By selectively applying bone growth promoting agent 1367 to region 1368, new bone growth may be facilitated between vertebral bodies 1422-1424, and within interbody spaces 1432-1433, eventually fusing vertebral bodies 1422-1424 together to provide maximum support.

Referring to FIG. 67, in some embodiments, plate 1361 may include first wide hole 1371 and second wide hole 1373. Wide holes 1371 and 1373 are preferably associated with region 1368, where new bone growth is expected to take place. Because plate 1361 is often comprised of metal, it may be difficult for a surgeon to observe new bone growth with an x-ray under plate 1361. Therefore, wide holes 1371 and 1373 provide the surgeon with an easy way to observe new bone growth along region 1368, or between vertebral bodies 1422-1424.

The illustrated embodiment is merely an example and it can be imagined that the plate spans a plurality of vertebral bodies having a plurality of regions that are aligned with the interbody spaces between vertebral bodies. These regions may include one or more bone growth promoting agents. Additionally, there may be a plurality of regions that do not contain bone growth promoting agents.

In some cases, following surgical correction along the lamina region of the vertebral body, it may be necessary to increase the diameter of the spinal canal. Preferably, a spinal fixation system may include provisions that may be used to increase the diameter of a spinal canal as well as to promote new bone growth. This widened canal configuration may allow for an increase in new bone growth over the originally narrow canal.

Figure 68:
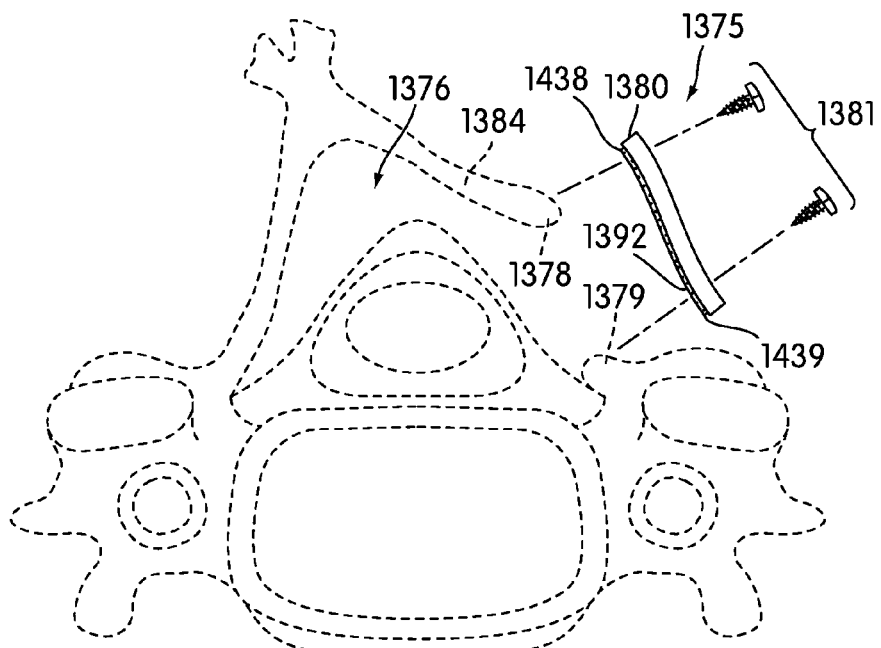
FIG. 68 is a top view of a preferred embodiment of a plate with selectively applied bone growth promoting agents.

FIG. 68 is an exploded view of spinal fixation system 1375. In this embodiment, spinal fixation system 1375 includes plate 1380. Plate 1380 may be any type of plate, including plates similar to those previously discussed. In general, plate 1380 may have any shape and/or size. Preferably plate 1380 is shaped to fit on the side of spinal canal 1376.

Spinal fixation system 1375 further includes screw set 1381. The screws comprising screw set 1381 may be any type of screw configured to insert into bone. Generally, the number of screws in screw set 1381 may vary. In a preferred embodiment, screw set 1381 includes two screws.

Preferably, plate 1380 and screw set 1381 may be associated with vertebral lamina 1384. In this embodiment, vertebral lamina 1384 has been split to increase the diameter of spinal canal 1376. Preferably, plate 1380 is oriented in a manner so that it attaches to first end 1378 and second end 1379 of vertebral lamina 1384.

Preferably, spinal fixation system 1375 includes provisions for promoting bone growth on vertebral lamina 1384. In a preferred embodiment, one or more bone growth promoting agents may be associated with plate 1380. Generally, one or more bone growth promoting agents may be selectively applied to various regions of plate 1380. In this embodiment, bone growth promoting agent 1392 may be selectively applied to plate 1380 at first region 1438 and second region 1439, associated with screw set 1381. Additionally, in an alternative embodiment, one or more bone growth promoting agents may be associated with screw set 1381. In another embodiment, the bone growth promoting agent is applied to the entire outer surface of plate 1380.

Figure 69:
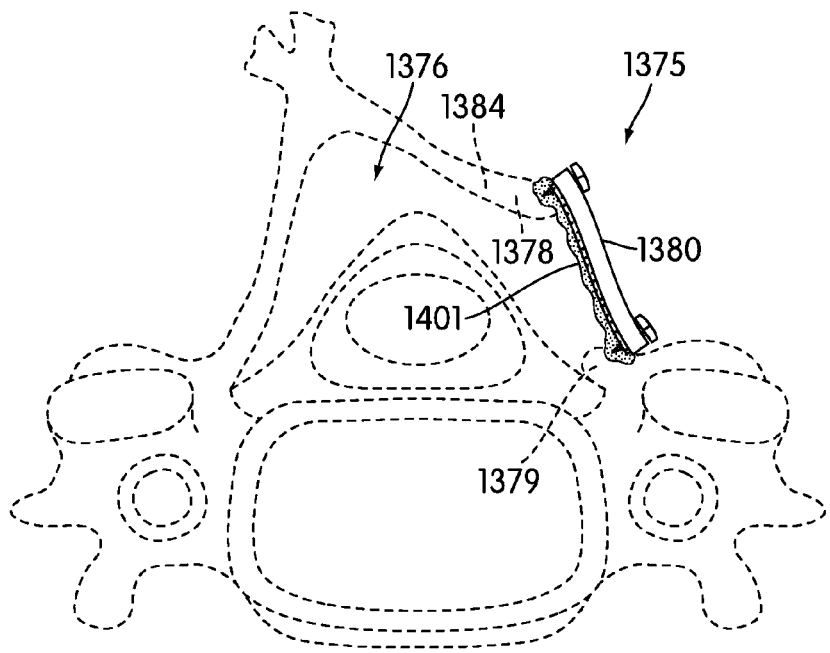
FIG. 69 is a top view of a preferred embodiment of a plate with bone growth.

Preferably, the regions including bone growth promoting agents include provisions for new bone fusion at vertebral lamina 1384 and plate 1380. As seen in FIG. 69, new bone growth 1401 can be observed on plate 1380. With this configuration, new bone growth 1401 on plate 1380 provides for fusion between first end 1378 and second end 1379 of vertebral lamina 1384. This preferably allows spinal canal 1376 to heal with a widened diameter, allowing for increased space of spinal canal 1376 while preserving spinal stability. Additionally, this preferred arrangement creates a rebar effect, reinforcing the strength of the connection between vertebral lamina 1384 and the vertebrae. This arrangement also helps to incorporate plate 1380 and screws comprising screw set 1381 into the bone or bones. This design is advantageous over previous technologies because its allows for the incorporation of plates or screws into the bone to augment fusion or healing, whereas previous technologies only allow for fixation of the bone members.

In some cases, a surgeon may need to apply one or more plates to the lateral portion of one or more vertebral bodies. This may be done in a similar manner to the use of plates on the anterior side of a set of vertebrae. Preferably, as with previous embodiments, the plates include provisions for promoting new bone growth or bony fusion at selected regions of the vertebrae.

Figure 70:
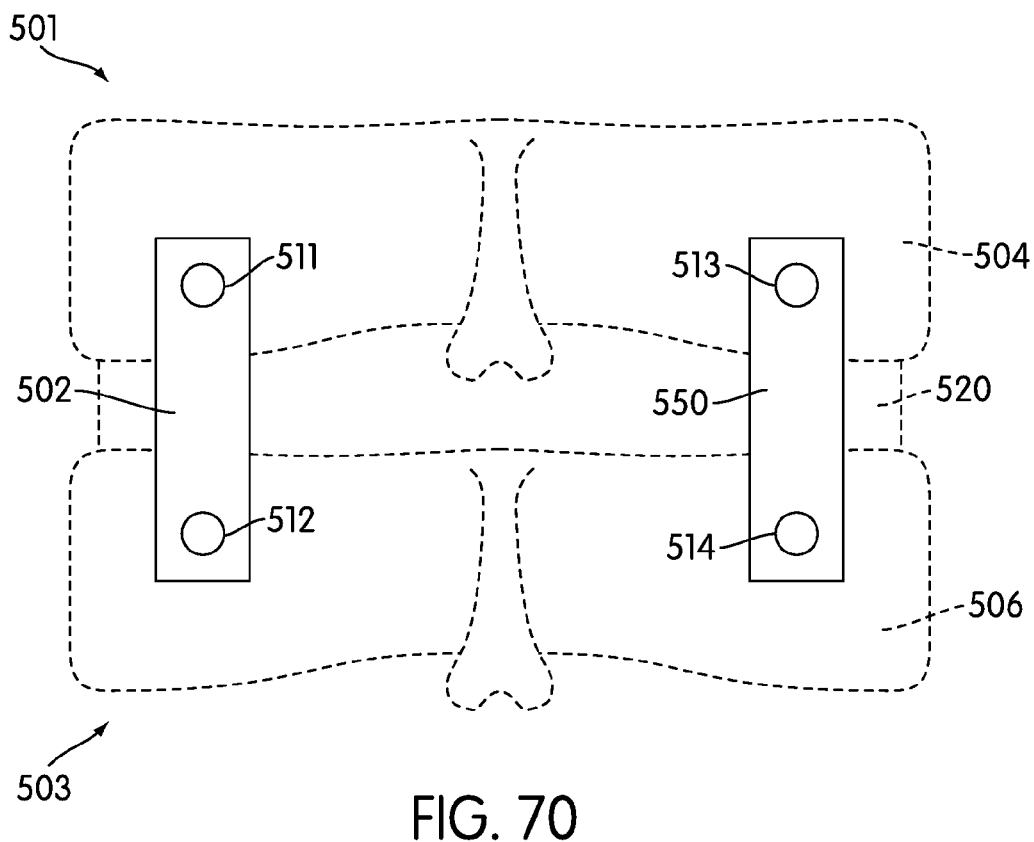
FIG. 70 is a posterior view of a preferred embodiment of a plate associated with the lateral side of two vertebral bodies.
Figure 71:
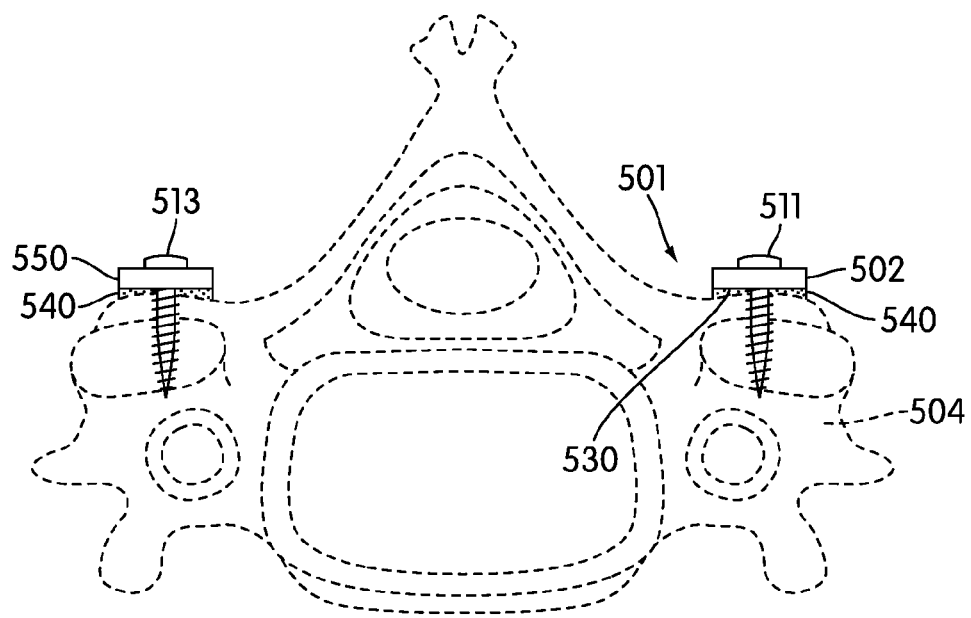
FIG. 71 is a top down view of a preferred embodiment of a plate associated with the lateral side of a vertebral body with bone growth

Referring to FIGS. 70-71, in some embodiments, first plate 502 may be disposed along first lateral portion 501 of first vertebral body 504 and first lateral portion 503 of second vertebral body 506. Likewise, second plate 550 may be disposed along second lateral portion 551 of first vertebral body 504 and second lateral portion 552 of second vertebral body 506. In the current embodiment, first vertebral body 504 may be a cervical, thoracic or lumbar vertebral body. Likewise, second vertebral body 506 may be a cervical, thoracic, lumbar or sacral vertebral body.

In some embodiments, first plate 502 is attached to first lateral portion 501 of first vertebral body 504 by first screw 511 and to first lateral portion 503 of second vertebral body 506 by second screw 512. Also, second plate 550 may be attached to second lateral portion 551 of first vertebral body 504 by third screw 513 and to second lateral portion 552 of second vertebral body 506 by fourth screw 514. Preferably, plates 502 and 550 each span space 520 that is disposed between first vertebral body 504 and second vertebral body 506. In some cases, space 520 may be filled in with bone or another substitute. With this configuration plates 502 and 550 may serve to hold first vertebral body 504 and second vertebral body 506 together, as well as help to keep any bone or other material in place within space 520.

Referring to FIG. 71, in a preferred embodiment, a bone growth promoting agent may be selectively applied to plates 502 and 550. In this embodiment, first side 530 of first plate 502 may include bone growth promoting agent 540. Likewise, first side 531 of second plate 550 may include bone growth promoting agent 540. Bone growth promoting agent 540 may be selectively applied to sides 530 and 531 in any manner, including the various patterns previously discussed. Using this arrangement, bone growth promoting agent 540 may help plates 502 and 550 fuse to vertebral bodies 504 and 506. Furthermore, new bone growth may be promoted between vertebral bodies 504 and 506 using this configuration.

This preferred arrangement creates a rebar effect, reinforcing the strength of the connection between adjacent vertebrae. This arrangement also helps to incorporate plates 502 and 550 into the bone or bones. This design is advantageous over previous technologies that only allow for fixation of adjacent vertebrae using one or more plates, but not the incorporation of the plates into the bone to augment fusion or healing.

In some embodiments, two adjacent vertebrae may be fused together using a single screw. In some cases, a surgeon may need to fuse the sacral vertebral body, or the sacrum, to the L5 vertebral body. This may be achieved, for example, by inserting a single screw through a portion of the L5 vertebral body and into a portion of the sacrum. Preferably, this screw may include a bone growth promoting agent to facilitate bone fusion between the L5 vertebral body and the sacrum. Additionally, in some cases, a single screw with a bone growth promoting agent may also be used to fuse two lumbar vertebrae together.

Figure 72:
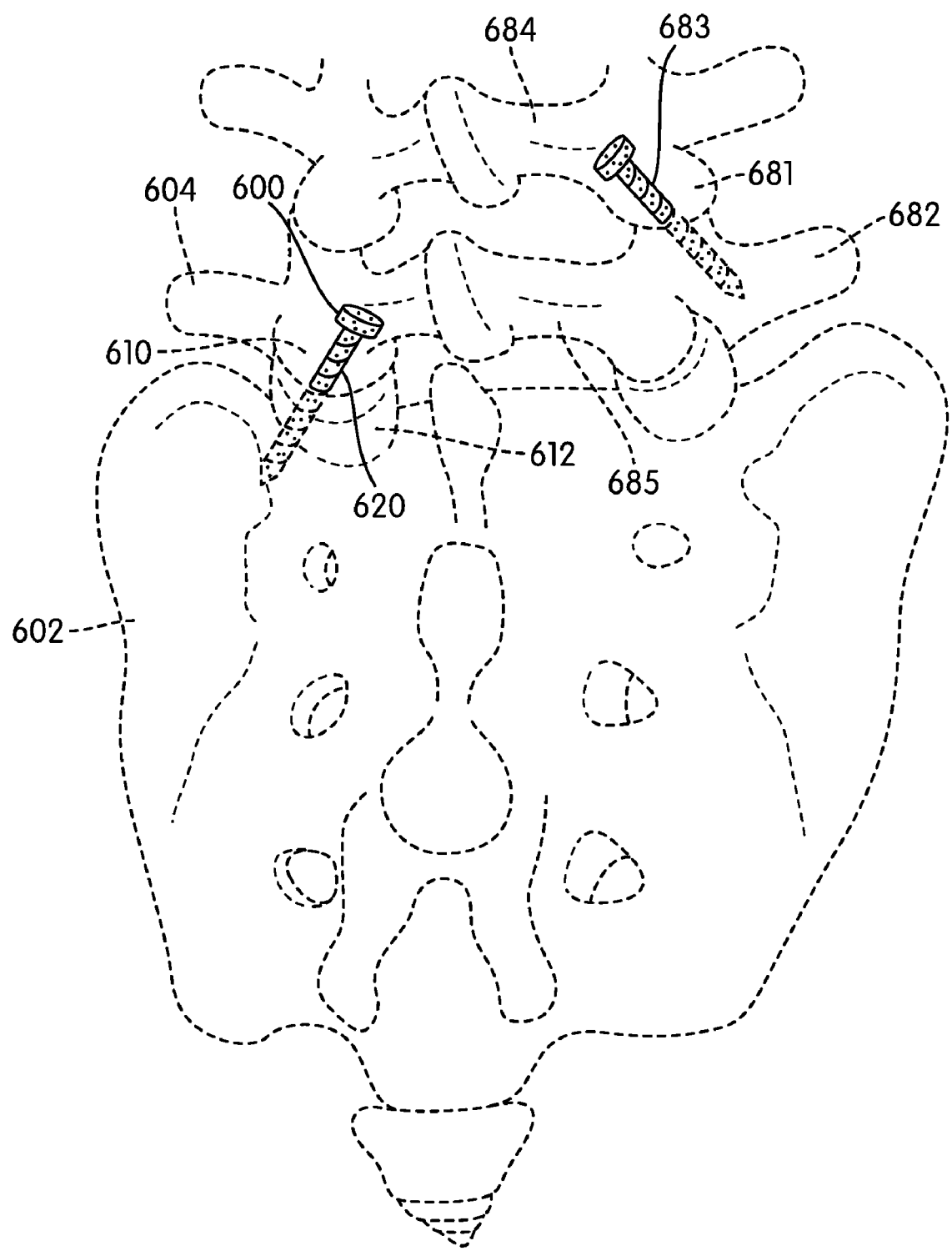
FIG. 72 is a posterior view of a preferred embodiment of one or more screws associated with the lumbar spine.

FIG. 72 is an isometric view of a preferred embodiment of first spinal screw 600 and second spinal screw 683. Spinal screws 600 and 683 may be any type of screw configured to insert into bone. In particular, as previously discussed, spinal screws 600 and 683 could be solid, hollow and/or cannulated. Spinal screws 600 and 683 may also include both macro and/or micro holes.

First spinal screw 600 is preferably associated with sacrum 602 and first vertebral body 604. In this preferred embodiment, first vertebral body 604 is the L5 vertebral body of the lumbar region of the spine. In some embodiments, first spinal screw 600 is inserted through facet joint 610 of first vertebral body 604 into pedicle 612 of sacrum 602. With this configuration, vertebral body 604 may be fastened into place with respect to sacrum 602.

Additionally, second spinal screw 683 is preferably associated with first vertebral body 604 and second vertebral body 684. In this preferred embodiment, second vertebral body 684 may be the L4 vertebral body of the lumbar region of the spine. In some embodiments, second spinal screw 683 is inserted through facet joint 681 of second vertebral body 684 into pedicle 682 of first vertebral body 604. With this configuration, vertebral bodies 604 and 684 may be fastened together.

Preferably, spinal screws 600 and 683 include provisions for promoting bone growth. In some embodiments, spinal screws 600 and 683 may include selectively applied bone growth promoting agent 620. Bone growth promoting agent 620 may be any type of bone growth promoting agent. In other embodiments, spinal screws 600 and 683 may include multiple bone growth promoting agents. Bone growth promoting agent 620 may be selectively applied to any portions of screws 600 and 683, including the various portions of screws previously discussed with respect to screws in earlier embodiments.

Figure 73:
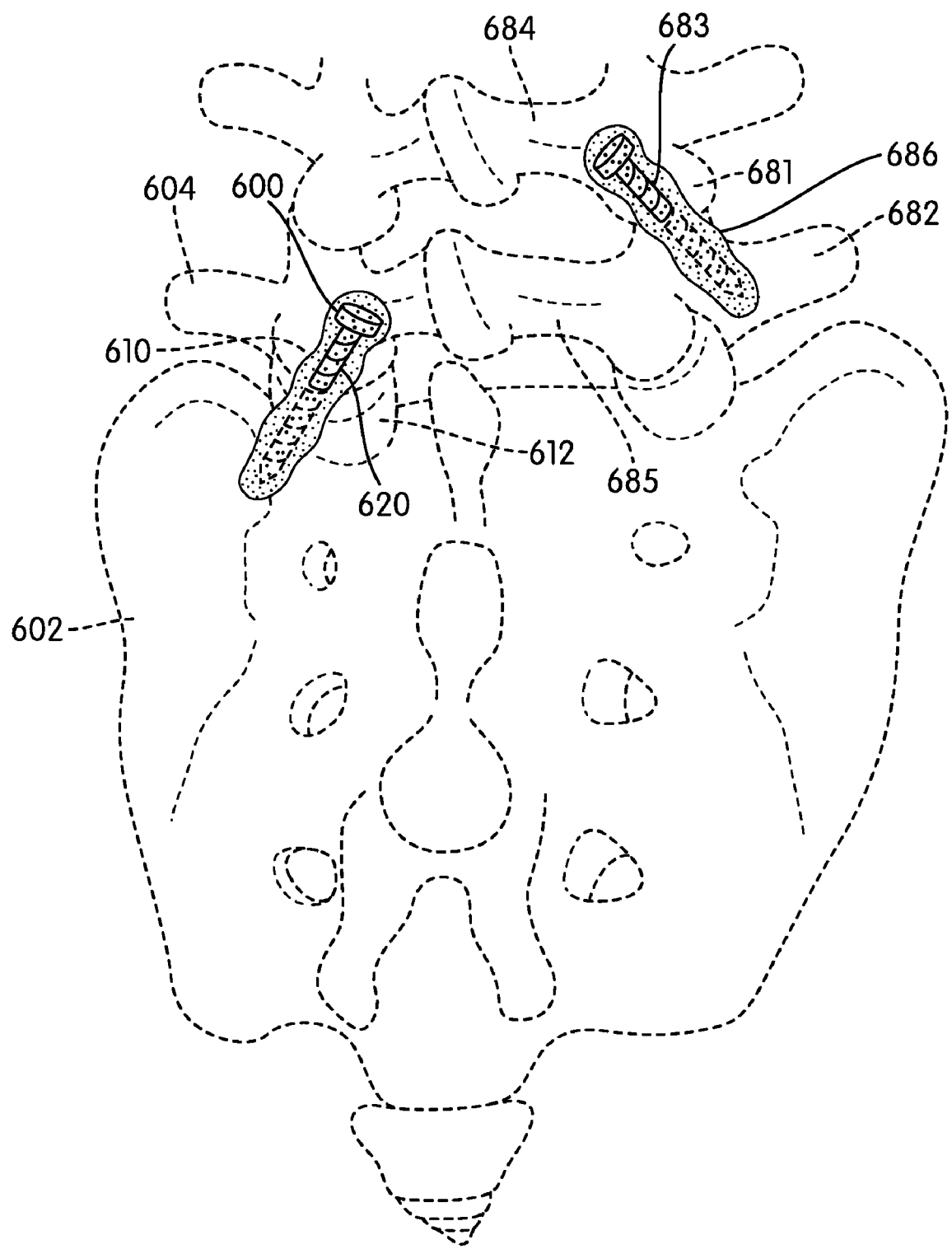
FIG. 73 is a posterior view of a preferred embodiment of one or more screws with bone growth in the lumbar spine.

Preferably, as seen in FIG. 73, new bone growth 650 may occur across first spinal screw 600 due to the presence of bone growth promoting agent 620. This preferred arrangement preferably creates a rebar effect, reinforcing the strength of the connection between sacrum 602 and vertebral body 604. Similarly, new bone growth 686 may occur across second screw 683 due to the presence of bone growth promoting agent 620. This preferred arrangement may also create a rebar effect, reinforcing the strength of the connection between vertebral bodies 604 and 684. This arrangement also helps to incorporate screws 600 and 683 into the bone or bones. This design is advantageous over previous technologies because it allows for the incorporation of the screw into the bone to augment fusion or healing, whereas previous technologies only allow for fixation of the spine.

In the current embodiment, second screw 683 is associated with vertebral bodies 604 and 684. However, in other embodiments, second screw 683 could be associated with other vertebral bodies as well. Generally, the configuration described here for fusing vertebral bodies 604 and 684 using second screw 683 and a selectively applied bone growth promoting agent could be used with any adjacent vertebrae in the cervical, lumbar, or thoracic areas of the spine. In some cases, more than two vertebrae could be fused using this method.

While various embodiments of the invention have been described, the description is intended to be exemplary, rather than limiting and it will be apparent to those of ordinary skill in the art that many more embodiments and implementations are possible that are within the scope of the invention. Accordingly, the invention is not to be restricted except in light of the attached claims and their equivalents. Also, various modifications and changes may be made within the scope of the attached claims.

We claim:

1. A spinal fixation system, comprising:
   a screw configured for implantation into at least one vertebral body;
   the screw including a screw body;
   a rod that is coupled to the screw using a coupling device;
   wherein the rod includes a first portion within the coupling device and a second exposed portion outside the coupling device, and wherein the second exposed portion of the rod includes a first region and a second region;
   wherein the first region of the second exposed portion of the rod is a first radial section of the rod and wherein the second region of the second exposed portion of the rod is a second remaining radial section of the rod;
   wherein the first radial section is limited to a portion of the rod that is visible when viewing the rod from a direction in which the screw extends from the rod;
   wherein the first region of the rod has bone growth promoting agent and the second region remains exposed without bone growth promoting agent;
   wherein the first region includes a first area having a bone growth promoting agent selectively applied in a first pattern and a second area having a bone growth promoting agent selectively applied in a second pattern; and
   wherein the first pattern is different from the second pattern.

2. The spinal fixation system according to claim 1, wherein the rod is associated with two or more screws, each screw including a screw body with a bone growth promoting agent selectively applied to the screw body.

3. The spinal fixation system according to claim 1, wherein the bone growth promoting agent is applied to the screw and the coupling device, and wherein the bone growth promoting agent extends from the first region of the rod, through the coupling device, and to the screw.

4. The spinal fixation system according to claim 1, wherein the first pattern comprises a striped pattern and the second pattern comprises a spotted pattern.

5. The spinal fixation system according to claim 1, wherein the rod is associated with multiple hooks and multiple connecting devices for fixing the hooks to the rod, and wherein the multiple hooks include a selectively applied bone growth promoting agent.

6. The bone fixation system according to claim 1, wherein the first pattern comprises a striped pattern and the second pattern comprises a striped pattern different from the striped pattern of the first pattern.

7. The spinal fixation system according to claim 1, wherein the bone growth promoting agent is applied to the first area in a spotted pattern comprising a plurality of spaced apart spots.

8. The spinal fixation system according to claim 7, wherein the spaced apart spots vary in shape.

9. The spinal fixation system according to claim 1, wherein the first radial section and the second radial section are approximately equal.

10. The spinal fixation system according to claim 1, wherein when the spinal fixation system is implanted in the at least one vertebral body, the first region of the second exposed portion of the rod is associated with an anterior side of the at least one vertebral body and the second region of the second exposed portion of the rod is associated with a posterior side of the at least one vertebral body.

11. The spinal fixation system according to claim 1, wherein the first area and the second area are longitudinally spaced apart.

12. The spinal fixation system according to claim 1, wherein the bone growth promoting agent is applied to the first area in a geometric pattern comprising a checkerboard.

13. The spinal fixation system according to claim 1, wherein the bone growth promoting agent of the first area is different from the bone growth promoting agent of the second area.

14. A spinal fixation system, comprising:
a first screw configured for implantation into a first vertebral body and a second screw configured for implantation into a second vertebral body;
the first screw and the second screw each including a first screw body and a second screw body;
a rod that is coupled to the first screw and the second screw using a first coupling device and a second coupling device,
wherein the rod includes a first portion within the first coupling device, a second portion within the second coupling device, and a third exposed portion between the first and second coupling devices, and wherein the third exposed portion of the rod includes a first region and a second region;
wherein a bone growth promoting agent is applied to the first and second screw bodies,
wherein the first region of the third exposed portion of the rod is a first radial section of the rod and wherein the second region of the third exposed portion of the rod is a second remaining radial section of the rod;
wherein the first radial section is limited to a portion of the rod that is visible when viewing the rod from a direction in which the screw extends from the rod;
wherein the first region of the rod has bone growth promoting agent and the second region remains exposed without bone growth promoting agent;
wherein the first region includes a first area having a bone growth promoting agent selectively applied in a first pattern and a second area having a bone growth promoting agent selectively applied in a second pattern; and
wherein the first pattern is different from the second pattern.

15. The spinal fixation system according to claim 14, wherein the first screw is associated with a first screw set that is configured for implantation into the second vertebral body.

16. The spinal fixation system according to claim 15, wherein the screws comprising the first screw set include screw bodies with a selectively applied bone growth promoting agent.

17. The spinal fixation system according to claim 14, wherein the second screw is associated with a second screw set that is configured for implantation into the first vertebral body.

18. The spinal fixation system according to claim 17, wherein the screws comprising the second screw set include screw bodies with a selectively applied bone growth promoting agent.

19. The spinal fixation system according to claim 14, wherein the bone growth promoting agent is applied to the first screw, the second screw, the first coupling device, and the second coupling device, and wherein the bone growth promoting agent extends from the first screw, through the first coupling device, through the first region of the rod, through the second coupling device, and to the second screw.

20. The spinal fixation system according to claim 14, wherein the first coupling device and the second coupling device include a bone growth promoting agent.

21. The spinal fixation system according to claim 14, wherein the first pattern comprises a striped pattern and the second pattern comprises a spotted pattern.

22. The spinal fixation system according to claim 14, wherein the first pattern comprises a striped pattern and the second pattern comprises a striped pattern different from the striped pattern of the first pattern.

23. The spinal fixation system according to claim 14, wherein the first radial section and the second radial section are approximately equal.

24. The spinal fixation system according to claim 14, wherein when the spinal fixation system is implanted in the first vertebral body, the first region of the third exposed portion of the rod is associated with an anterior side of the first vertebral body and the second region of the third exposed portion of the rod is associated with a posterior side of the first vertebral body.

25. The spinal fixation system according to claim 14, wherein the first area and the second area are longitudinally spaced apart.

26. The spinal fixation system according to claim 14, wherein the bone growth promoting agent is applied to the first area in a spotted pattern comprising a plurality of spaced apart spots.

27. The spinal fixation system according to claim 26, wherein the spaced apart spots vary in shape.

28. The spinal fixation system according to claim 14, wherein the bone growth promoting agent is applied to the first area in a geometric pattern comprising a checkerboard.

29. A spinal fixation system, comprising:
a screw configured for implantation into at least one vertebral body, the screw including a screw body;
a rod; and
a coupling device that couples the rod to the screw with the screw extending in a direction transverse to the rod,
wherein the rod includes a first covered portion within the coupling device and a second exposed portion outside the coupling device,
wherein the second exposed portion of the rod includes a first region and a second region,
wherein the first region of the second exposed portion of the rod is a first radial section of the rod and wherein the second region of the second exposed portion of the rod is a second remaining radial section of the rod;
wherein the first radial section is limited to a portion of the rod that is visible when viewing the rod from the transverse direction in which the screw extends from the rod;
wherein the first region of the rod has bone growth promoting agent and the second region remains exposed without bone growth promoting agent;
wherein the first region includes a first area having a bone growth promoting agent selectively applied in a first pattern and a second area having a bone growth promoting agent selectively applied in a second pattern; and
wherein the first pattern is different from the second pattern.

* * * * *